(12) United States Patent
Komp

(10) Patent No.: US 12,226,074 B2
(45) Date of Patent: *Feb. 18, 2025

(54) ENDOSCOPIC IMAGING WITH AUGMENTED PARALLAX

(71) Applicant: Covidien LP, Mansfield, MA (US)

(72) Inventor: John W. Komp, Dillon, CO (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/381,481

(22) Filed: Oct. 18, 2023

(65) Prior Publication Data

US 2024/0041298 A1    Feb. 8, 2024

Related U.S. Application Data

(63) Continuation of application No. 17/839,064, filed on Jun. 13, 2022, now Pat. No. 11,793,390, which is a
(Continued)

(51) Int. Cl.
*G06T 7/70* (2017.01)
*A61B 1/00* (2006.01)
(Continued)

(52) U.S. Cl.
CPC ...... *A61B 1/0005* (2013.01); *A61B 1/000094* (2022.02); *A61B 1/00194* (2022.02);
(Continued)

(58) Field of Classification Search
CPC ............ A61B 90/361; A61B 2090/364; A61B 2090/373; A61B 1/00193; A61B 1/3132;
(Continued)

(56) References Cited

U.S. PATENT DOCUMENTS

| | | | |
|---|---|---|---|
| 5,057,494 A | 10/1991 | Sheffield | |
| 5,321,113 A | 6/1994 | Cooper et al. | |

(Continued)

FOREIGN PATENT DOCUMENTS

| | | |
|---|---|---|
| BR | 0013237 A | 7/2003 |
| BR | 0116004 A | 6/2004 |

(Continued)

OTHER PUBLICATIONS

Communication pursuant to Article 94(3) EPC issued in European Patent Application No. 20150911.4 dated Mar. 4, 2022, 8 pages.
(Continued)

*Primary Examiner* — Howard D Brown, Jr.
(74) *Attorney, Agent, or Firm* — Weber Rosselli & Cannon LLP

(57) ABSTRACT

A method for imaging involves scanning an anatomical object within a patient and capturing reflected IR light with a plurality of cameras that are separate from the scanner. The IR images captured by the IR cameras are associated together to create an integrated image based on parallax between the IR cameras and the scanner. The integrated image is associated with a separate or optical light image of the anatomical object to generate an intra-operative 3D image that can be created in real-time. Systems for effectuating such imaging may include multiple surgical instruments supporting various cameras positioned to capture different fields of view and to increase parallax.

20 Claims, 13 Drawing Sheets

Related U.S. Application Data continuation of application No. 16/707,280, filed on Dec. 9, 2019, now Pat. No. 11,357,593.

(60) Provisional application No. 62/790,839, filed on Jan. 10, 2019.

(51) Int. Cl.
*A61B 1/04* (2006.01)
*A61B 90/00* (2016.01)
*G06T 7/00* (2017.01)

(52) U.S. Cl.
CPC .............. *A61B 1/046* (2022.02); *A61B 90/37* (2016.02); *G06T 7/0012* (2013.01); *A61B 2090/365* (2016.02); *A61B 2090/367* (2016.02); *A61B 2090/371* (2016.02); *G06T 2207/10028* (2013.01); *G06T 2207/10048* (2013.01); *G06T 2207/10068* (2013.01); *G06T 2211/428* (2013.01)

(58) Field of Classification Search
CPC ... A61B 1/04; A61B 1/0005; A61B 1/000094; A61B 1/00194; A61B 1/046; A61B 90/37; A61B 2090/365; A61B 2090/367; G06T 7/0012

See application file for complete search history.

(56) References Cited

U.S. PATENT DOCUMENTS

| | | | |
|---|---|---|---|
| 6,003,517 A | 12/1999 | Sheffield et al. |
| 6,009,189 A | 12/1999 | Schaack |
| 6,139,490 A | 10/2000 | Breidenthal et al. |
| 7,170,677 B1 | 1/2007 | Bendall et al. |
| 7,277,120 B2 | 10/2007 | Gere et al. |
| 7,564,626 B2 | 7/2009 | Bendall et al. |
| 7,812,815 B2 | 10/2010 | Banerjee et al. |
| 8,335,359 B2 | 12/2012 | Fidrich et al. |
| 8,442,355 B2 | 5/2013 | Imai |
| 8,508,580 B2 | 8/2013 | McNamer et al. |
| 8,706,184 B2 | 4/2014 | Mohr et al. |
| 8,827,934 B2 | 9/2014 | Chopra et al. |
| 8,922,589 B2 | 12/2014 | Laor |
| 9,005,112 B2 | 4/2015 | Hasser et al. |
| 9,044,138 B2 | 6/2015 | Sjostrom et al. |
| 9,066,086 B2 | 6/2015 | Angot et al. |
| 9,134,534 B2 | 9/2015 | Border et al. |
| 9,179,822 B2 | 11/2015 | Kitamura et al. |
| 9,182,596 B2 | 11/2015 | Border et al. |
| 9,188,765 B2 | 11/2015 | Venkataraman et al. |
| 9,223,138 B2 | 12/2015 | Bohn |
| 9,265,572 B2 | 2/2016 | Fuchs et al. |
| 9,277,201 B2 | 3/2016 | Izawa et al. |
| 9,285,589 B2 | 3/2016 | Osterhout et al. |
| 9,288,472 B2 | 3/2016 | Aoki et al. |
| 9,294,672 B2 | 3/2016 | Georgiev et al. |
| 9,364,294 B2 | 6/2016 | Razzaque et al. |
| 9,368,546 B2 | 6/2016 | Fleck et al. |
| 9,375,133 B2 | 6/2016 | Kitamura et al. |
| 9,375,268 B2 | 6/2016 | Long |
| 9,380,292 B2 | 6/2016 | McNamer et al. |
| 9,386,222 B2 | 7/2016 | Georgiev et al. |
| 9,473,766 B2 | 10/2016 | Douglas et al. |
| 9,479,755 B2 | 10/2016 | Routhier et al. |
| 9,485,496 B2 | 11/2016 | Venkataraman et al. |
| 9,554,117 B2 | 1/2017 | Lee et al. |
| 9,576,369 B2 | 2/2017 | Venkataraman et al. |
| 9,578,259 B2 | 2/2017 | Molina |
| 9,578,318 B2 | 2/2017 | Fleck et al. |
| 9,581,820 B2 | 2/2017 | Robbins |
| 9,684,174 B2 | 6/2017 | Fleck et al. |
| 9,712,759 B2 | 7/2017 | Venkataraman et al. |
| 9,717,981 B2 | 8/2017 | Robbins et al. |
| 9,730,572 B2 | 8/2017 | Hasser et al. |
| 9,733,458 B2 | 8/2017 | Georgiev et al. |
| 9,741,118 B2 | 8/2017 | Mullis |
| 9,749,547 B2 | 8/2017 | Venkataraman et al. |
| 9,759,917 B2 | 9/2017 | Osterhout et al. |
| 9,766,441 B2 | 9/2017 | Rappel |
| 9,779,643 B2 | 10/2017 | Bohn et al. |
| 9,807,381 B2 | 10/2017 | Fleck et al. |
| 9,807,382 B2 | 10/2017 | Duparre et al. |
| 9,813,616 B2 | 11/2017 | Lelescu et al. |
| 9,832,381 B2 | 11/2017 | Osborne |
| 9,843,723 B2 | 12/2017 | Osborne |
| 9,857,591 B2 | 1/2018 | Welch et al. |
| 9,858,673 B2 | 1/2018 | Ciurea et al. |
| 9,898,866 B2 | 2/2018 | Fuchs et al. |
| 9,918,659 B2 | 3/2018 | Chopra et al. |
| 9,986,224 B2 | 5/2018 | Mullis |
| 10,004,558 B2 | 6/2018 | Long et al. |
| 10,009,538 B2 | 6/2018 | Venkataraman et al. |
| 10,019,816 B2 | 7/2018 | Venkataraman et al. |
| 10,027,901 B2 | 7/2018 | Venkataraman et al. |
| 10,084,958 B2 | 9/2018 | Georgiev et al. |
| 10,091,405 B2 | 10/2018 | Molina |
| 10,105,034 B2 | 10/2018 | Suga |
| 10,122,993 B2 | 11/2018 | Venkataraman et al. |
| 10,127,682 B2 | 11/2018 | Mullis |
| 10,142,560 B2 | 11/2018 | Venkataraman et al. |
| 10,192,358 B2 | 1/2019 | Robbins |
| 10,194,897 B2 | 2/2019 | Cedro et al. |
| 10,234,687 B2 | 3/2019 | Welch et al. |
| 10,258,426 B2 | 4/2019 | Silva et al. |
| 10,262,453 B2 | 4/2019 | Mountney et al. |
| 10,299,880 B2 | 5/2019 | Luna et al. |
| 10,306,120 B2 | 5/2019 | Duparre |
| 10,317,690 B2 | 6/2019 | Cheng |
| 10,334,241 B2 | 6/2019 | Duparre et al. |
| 10,341,643 B2 | 7/2019 | Routhier et al. |
| 10,345,582 B2 | 7/2019 | Schneider et al. |
| 10,366,472 B2 | 7/2019 | Lelescu et al. |
| 10,373,719 B2 | 8/2019 | Soper et al. |
| 10,376,178 B2 | 8/2019 | Chopra |
| 10,380,752 B2 | 8/2019 | Ciurea et al. |
| 10,386,636 B2 | 8/2019 | Welch |
| 10,388,073 B2 | 8/2019 | Westerinen et al. |
| 10,397,560 B2 | 8/2019 | Miyao et al. |
| 10,398,513 B2 | 9/2019 | Razzaque et al. |
| 10,405,753 B2 | 9/2019 | Sorger |
| 10,412,314 B2 | 9/2019 | McMahon et al. |
| 10,413,369 B2 | 9/2019 | Kashima et al. |
| 10,430,682 B2 | 10/2019 | Venkataraman et al. |
| 10,444,931 B2 | 10/2019 | Akeley |
| 10,448,692 B2 | 10/2019 | Hsu |
| 10,462,362 B2 | 10/2019 | Lelescu et al. |
| 10,478,162 B2 | 11/2019 | Barbagli et al. |
| 10,478,717 B2 | 11/2019 | Robbins et al. |
| 10,480,926 B2 | 11/2019 | Froggatt et al. |
| 10,502,876 B2 | 12/2019 | Robbins et al. |
| 10,506,920 B2 | 12/2019 | Hasser et al. |
| 10,516,879 B2 | 12/2019 | Eash et al. |
| 10,524,866 B2 | 1/2020 | Srinivasan et al. |
| 10,540,818 B2 | 1/2020 | Akeley |
| 10,546,424 B2 | 1/2020 | Pang et al. |
| 10,547,772 B2 | 1/2020 | Molina |
| 10,548,459 B2 | 2/2020 | Itkowitz et al. |
| 10,555,788 B2 | 2/2020 | Panescu et al. |
| 10,567,464 B2 | 2/2020 | Pang et al. |
| 10,569,071 B2 | 2/2020 | Harris et al. |
| 10,598,914 B2 | 3/2020 | Siegel et al. |
| 10,603,106 B2 | 3/2020 | Weide et al. |
| 10,603,133 B2 | 3/2020 | Wang et al. |
| 10,610,306 B2 | 4/2020 | Chopra |
| 10,614,555 B2 | 4/2020 | Fukazawa et al. |
| 10,627,632 B2 | 4/2020 | Welch et al. |
| 10,638,099 B2 | 4/2020 | Mullis et al. |
| 10,638,953 B2 | 5/2020 | Duindam et al. |
| 10,639,114 B2 | 5/2020 | Schuh et al. |
| 10,674,138 B2 | 6/2020 | Venkataraman et al. |
| 10,674,970 B2 | 6/2020 | Averbuch et al. |
| 10,682,070 B2 | 6/2020 | Duindam |

(56) References Cited

U.S. PATENT DOCUMENTS

| | | | |
|---|---|---|---|
| 10,702,137 B2 | 7/2020 | Deyanov | |
| 10,706,543 B2 | 7/2020 | Donhowe et al. | |
| 10,709,506 B2 | 7/2020 | Coste-Maniere et al. | |
| 10,772,485 B2 | 9/2020 | Schlesinger et al. | |
| 10,796,432 B2 | 10/2020 | Mintz et al. | |
| 10,823,627 B2 | 11/2020 | Sanborn et al. | |
| 10,827,913 B2 | 11/2020 | Ummalaneni et al. | |
| 10,835,153 B2 | 11/2020 | Rafii-Tari et al. | |
| 10,885,630 B2 | 1/2021 | Li et al. | |
| 11,357,593 B2 * | 6/2022 | Komp | A61B 90/361 |
| 11,432,828 B1 * | 9/2022 | Lang | G16H 70/20 |
| 11,521,345 B2 * | 12/2022 | Jiang | G01S 7/52084 |
| 11,553,969 B1 * | 1/2023 | Lang | G06T 7/0012 |
| 11,793,390 B2 * | 10/2023 | Komp | A61B 1/00194 |
| 2002/0147462 A1 | 10/2002 | Mair et al. | |
| 2003/0013972 A1 | 1/2003 | Makin | |
| 2004/0120981 A1 | 6/2004 | Nathan | |
| 2008/0045938 A1 | 2/2008 | Weide et al. | |
| 2013/0303945 A1 | 11/2013 | Blumenkranz et al. | |
| 2014/0035798 A1 | 2/2014 | Kawada et al. | |
| 2015/0077529 A1 | 3/2015 | Hatta et al. | |
| 2015/0148690 A1 | 5/2015 | Chopra et al. | |
| 2015/0265368 A1 | 9/2015 | Chopra et al. | |
| 2016/0157939 A1 | 6/2016 | Larkin et al. | |
| 2016/0183841 A1 | 6/2016 | Duindam et al. | |
| 2016/0192860 A1 | 7/2016 | Allenby et al. | |
| 2016/0287344 A1 | 10/2016 | Donhowe et al. | |
| 2017/0112571 A1 | 4/2017 | Thiel et al. | |
| 2017/0112576 A1 | 4/2017 | Coste-Maniere et al. | |
| 2017/0209071 A1 | 7/2017 | Zhao et al. | |
| 2017/0265952 A1 | 9/2017 | Donhowe et al. | |
| 2017/0311844 A1 | 11/2017 | Zhao et al. | |
| 2017/0319165 A1 | 11/2017 | Averbuch | |
| 2018/0078318 A1 | 3/2018 | Barbagli et al. | |
| 2018/0144092 A1 | 5/2018 | Flitsch et al. | |
| 2018/0153621 A1 | 6/2018 | Duindam et al. | |
| 2018/0235709 A1 | 8/2018 | Donhowe et al. | |
| 2018/0240237 A1 | 8/2018 | Donhowe et al. | |
| 2018/0256262 A1 | 9/2018 | Duindam et al. | |
| 2018/0263706 A1 | 9/2018 | Averbuch | |
| 2018/0279852 A1 | 10/2018 | Rafii-Tari et al. | |
| 2018/0325419 A1 | 11/2018 | Zhao et al. | |
| 2019/0000559 A1 | 1/2019 | Berman et al. | |
| 2019/0000560 A1 | 1/2019 | Berman et al. | |
| 2019/0008413 A1 | 1/2019 | Duindam et al. | |
| 2019/0038365 A1 | 2/2019 | Soper et al. | |
| 2019/0065209 A1 | 2/2019 | Mishra et al. | |
| 2019/0110839 A1 | 4/2019 | Rafii-Tari et al. | |
| 2019/0175062 A1 | 6/2019 | Rafii-Tari et al. | |
| 2019/0175799 A1 | 6/2019 | Hsu et al. | |
| 2019/0183318 A1 | 6/2019 | Froggatt et al. | |
| 2019/0183585 A1 | 6/2019 | Rafii-Tari et al. | |
| 2019/0183587 A1 | 6/2019 | Rafii-Tari et al. | |
| 2019/0192234 A1 | 6/2019 | Gadda et al. | |
| 2019/0209016 A1 | 7/2019 | Herzlinger et al. | |
| 2019/0209043 A1 | 7/2019 | Zhao et al. | |
| 2019/0216548 A1 | 7/2019 | Ummalaneni | |
| 2019/0239723 A1 | 8/2019 | Duindam et al. | |
| 2019/0239831 A1 | 8/2019 | Chopra | |
| 2019/0250050 A1 | 8/2019 | Sanborn et al. | |
| 2019/0254649 A1 | 8/2019 | Walters et al. | |
| 2019/0269470 A1 | 9/2019 | Barbagli et al. | |
| 2019/0269818 A1 | 9/2019 | Dhanaraj et al. | |
| 2019/0269819 A1 | 9/2019 | Dhanaraj et al. | |
| 2019/0272634 A1 | 9/2019 | Li et al. | |
| 2019/0298160 A1 | 10/2019 | Ummalaneni et al. | |
| 2019/0298451 A1 | 10/2019 | Wong et al. | |
| 2019/0320878 A1 | 10/2019 | Duindam et al. | |
| 2019/0320937 A1 | 10/2019 | Duindam et al. | |
| 2019/0336238 A1 | 11/2019 | Yu et al. | |
| 2019/0343424 A1 | 11/2019 | Blumenkranz et al. | |
| 2019/0350659 A1 | 11/2019 | Wang et al. | |
| 2019/0365199 A1 | 12/2019 | Zhao et al. | |
| 2019/0365479 A1 | 12/2019 | Rafii-Tari | |
| 2019/0365486 A1 | 12/2019 | Srinivasan et al. | |
| 2019/0380787 A1 | 12/2019 | Ye et al. | |
| 2020/0000319 A1 | 1/2020 | Saadat et al. | |
| 2020/0000526 A1 | 1/2020 | Zhao | |
| 2020/0008655 A1 | 1/2020 | Schlesinger et al. | |
| 2020/0030044 A1 | 1/2020 | Wang et al. | |
| 2020/0030461 A1 | 1/2020 | Sorger | |
| 2020/0038750 A1 | 2/2020 | Kojima | |
| 2020/0043207 A1 | 2/2020 | Lo et al. | |
| 2020/0046431 A1 | 2/2020 | Soper et al. | |
| 2020/0046436 A1 | 2/2020 | Tzeisler et al. | |
| 2020/0054399 A1 | 2/2020 | Duindam et al. | |
| 2020/0054408 A1 | 2/2020 | Schuh et al. | |
| 2020/0060771 A1 | 2/2020 | Lo et al. | |
| 2020/0069192 A1 | 3/2020 | Sanborn et al. | |
| 2020/0077870 A1 | 3/2020 | Dicarlo et al. | |
| 2020/0078023 A1 | 3/2020 | Cedro et al. | |
| 2020/0078095 A1 | 3/2020 | Chopra et al. | |
| 2020/0078103 A1 | 3/2020 | Duindam et al. | |
| 2020/0085514 A1 | 3/2020 | Blumenkranz | |
| 2020/0109124 A1 | 4/2020 | Pomper et al. | |
| 2020/0129045 A1 | 4/2020 | Prisco | |
| 2020/0129239 A1 | 4/2020 | Bianchi et al. | |
| 2020/0138514 A1 | 5/2020 | Blumenkranz et al. | |
| 2020/0138515 A1 | 5/2020 | Wong | |
| 2020/0138518 A1 | 5/2020 | Lang | |
| 2020/0142013 A1 | 5/2020 | Wong | |
| 2020/0155116 A1 | 5/2020 | Donhowe et al. | |
| 2020/0155232 A1 | 5/2020 | Wong | |
| 2020/0170623 A1 | 6/2020 | Averbuch | |
| 2020/0170720 A1 | 6/2020 | Ummalaneni | |
| 2020/0179058 A1 | 6/2020 | Barbagli et al. | |
| 2020/0188021 A1 | 6/2020 | Wong et al. | |
| 2020/0188032 A1 * | 6/2020 | Komp | A61B 1/00042 |
| 2020/0188038 A1 | 6/2020 | Donhowe et al. | |
| 2020/0195903 A1 * | 6/2020 | Komp | A61B 1/0661 |
| 2020/0205903 A1 | 7/2020 | Srinivasan et al. | |
| 2020/0205904 A1 | 7/2020 | Chopra | |
| 2020/0214664 A1 | 7/2020 | Zhao et al. | |
| 2020/0222146 A1 * | 7/2020 | Komp | A61B 1/0005 |
| 2020/0229679 A1 | 7/2020 | Zhao et al. | |
| 2020/0242767 A1 | 7/2020 | Zhao et al. | |
| 2020/0249428 A1 * | 8/2020 | Sugiyama | H04N 23/671 |
| 2020/0275860 A1 | 9/2020 | Duindam | |
| 2020/0297442 A1 | 9/2020 | Adebar et al. | |
| 2020/0315554 A1 | 10/2020 | Averbuch et al. | |
| 2020/0330795 A1 | 10/2020 | Sawant et al. | |
| 2020/0352427 A1 | 11/2020 | Deyanov | |
| 2020/0364865 A1 | 11/2020 | Donhowe et al. | |
| 2020/0383750 A1 | 12/2020 | Kemp et al. | |
| 2021/0000524 A1 | 1/2021 | Barry et al. | |

FOREIGN PATENT DOCUMENTS

| | | |
|---|---|---|
| BR | 0307259 A | 12/2004 |
| BR | 0412298 A2 | 9/2006 |
| BR | 112018003862 A2 | 10/2018 |
| CZ | 1644519 A | 12/2008 |
| CZ | 486540 B1 | 9/2016 |
| CZ | 2709512 B6 | 8/2017 |
| CZ | 2884879 B1 | 1/2020 |
| DE | 102011084920 A1 | 4/2013 |
| EP | 1644519 B1 | 12/2008 |
| EP | 2141497 A1 | 1/2010 |
| EP | 3413830 A4 | 9/2019 |
| EP | 3478161 A4 | 2/2020 |
| EP | 3641686 A2 | 4/2020 |
| EP | 3644885 A1 | 5/2020 |
| EP | 3644886 A1 | 5/2020 |
| EP | 3749239 A1 | 12/2020 |
| MX | 03005028 A | 1/2004 |
| MX | 03000137 A | 9/2004 |
| MX | 03006874 A | 9/2004 |
| MX | 225663 B | 1/2005 |
| MX | 226292 B | 2/2005 |
| MX | 03010507 A | 7/2005 |
| MX | 05011725 A | 5/2006 |
| MX | 06011286 A | 3/2007 |
| MX | 246862 B | 6/2007 |
| MX | 2007006441 A | 8/2007 |

(56) References Cited

FOREIGN PATENT DOCUMENTS

| | | |
|---|---|---|
| MX | 265247 B | 3/2009 |
| MX | 284569 B | 3/2011 |
| WO | 2018032804 A1 | 2/2018 |
| WO | 2018049215 A1 | 3/2018 |
| WO | WO-2018132804 A1 * | 7/2018 ........... A61B 17/155 |

OTHER PUBLICATIONS

Communication pursuant to Article 94(3) EPC issued in European Patent Application No. 20150911.4 dated May 19, 2023.

* cited by examiner

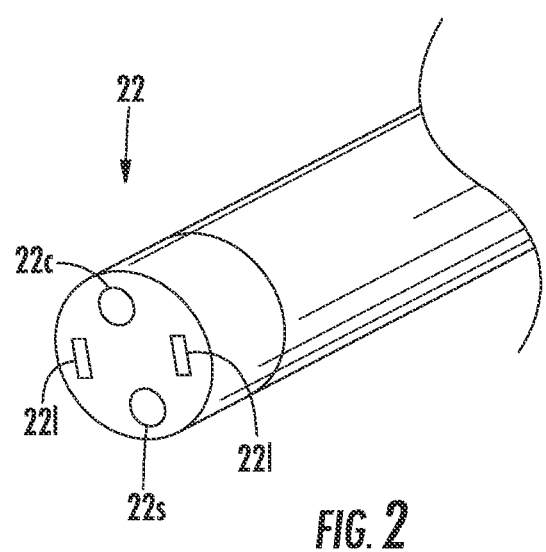

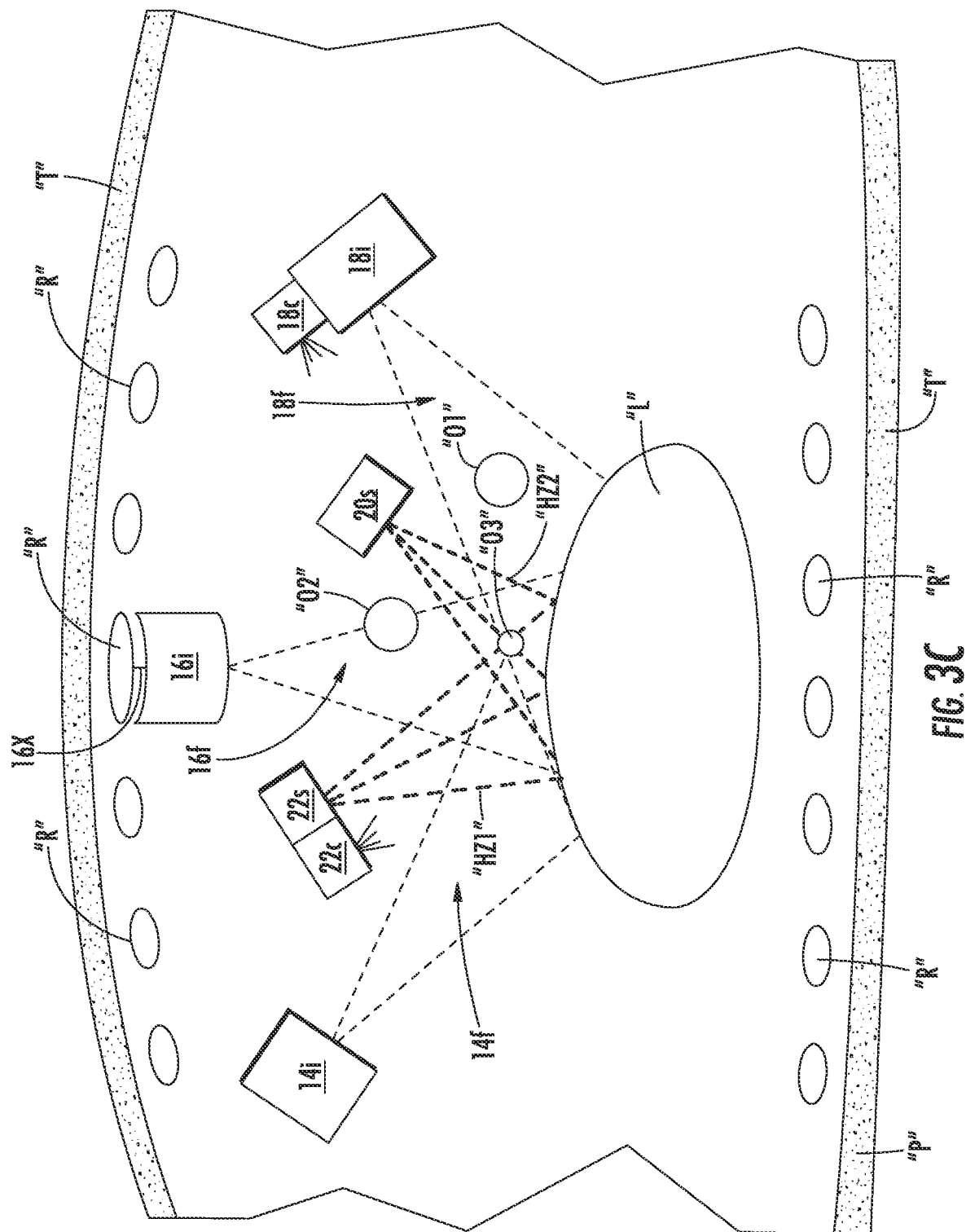

ENDOSCOPIC IMAGING WITH AUGMENTED PARALLAX

CROSS-REFERENCE TO RELATED APPLICATION

This application is a continuation of U.S. patent application Ser. No. 17/839,064, filed on Jun. 13, 2022, which is a continuation of U.S. patent application Ser. No. 16/707,280, filed on Dec. 9, 2019, now U.S. Pat. No. 11,357,593 which claims the benefit of and priority to U.S. Provisional Patent Application No. 62/790,839, filed on Jan. 10, 2019, the entire disclosure of each of which is incorporated by reference herein.

BACKGROUND

Description of Related Art

Current monocular optical devices (e.g. endoscope, bronchoscope, colonoscope) used for viewing surgical fields during minimally invasive surgery (e.g. laparoscopy) and visual diagnostic procedures (e.g. colonoscopy, bronchoscopy) provide limited reference information on the absolute position of surgical tools and anatomical features because the image has no depth of field. Binocular (also known as stereoscopic) optical devices provide limited depth of field affording the surgeon visual information on the distance between items within the optical device's field of view. The accuracy of distance information is limited based on the amount of parallax provided by the optical paths, determined by the distance between the optical paths, and the amount of overlap between the two optical paths.

SUMMARY

This disclosure is directed to a method of imaging within a body of a patient. The method includes capturing IR light reflected off of an anatomical object with at least two IR cameras, with the at least two IR cameras positioned in spaced relation relative to a scanner projecting the IR light. The method further includes generating a plurality of IR light images, where each IR light image of the plurality of IR light images is generated based on IR light captured by a respective IR camera of the at least two IR cameras. Additionally, the method includes determining a parallax of each IR camera with respect to the scanner, associating each IR light image of the plurality of IR light images with each other based on the determined parallax to create an integrated IR light image, associating the integrated IR light image with an optical light image captured by an optical light camera, generating an intra-operative 3D image based on the association of the integrated IR light image with the optical light image, and displaying the generated intra-operative 3D image on a display.

Associating each IR light image of the plurality of IR light images with each other may include generating a 3D point cloud. In an embodiment, the at least two IR cameras include three IR cameras arrayed in the body of the patient, and capturing IR light reflected off the anatomical object includes capturing IR light with the three IR cameras. Each IR camera may have a different field of view. The different fields of view may overlap.

In an embodiment, a first IR camera of the at least two IR cameras is coupled to a first surgical instrument and a second IR camera of the at least two IR cameras is coupled to a second surgical instrument, and capturing IR light reflected off of the anatomical object includes capturing IR light reflected off of the anatomical object within a first field of view and a second field of view. The first field of view is associated with the first IR camera and the second field of view is associated with the second IR camera. The method may further include overlapping the first and second fields of view.

In an embodiment, the method further includes projecting IR light with a second scanner onto the anatomical object within the patient at a different frequency, interleaved timing, or combinations thereof, then that of the IR light projected by the scanner.

Additionally, or alternatively, generating the intra-operative 3D image is effectuated in real-time and updated as new optical light images are captured by the optical light camera.

According to another aspect of the disclosure, a system for imaging within a body of a patient includes: an optical camera; a surgical device having a scanner configured to transmit infrared (IR) light within the body of the patient; a first surgical instrument having a first IR camera; a second surgical instrument having a second IR camera; and a computing device. The first and second surgical instruments are separate from the surgical device such that the first and second IR cameras are disposed in spaced relationship with each other and the scanner. The computing device is in communication with the scanner and the first and second IR cameras. The computing device has a processor and a memory storing instructions thereon which, when executed on the processor, cause the system to: determine parallax between the first and second IR cameras with respect to each other and the scanner; generate an integrated IR image based on the determined parallax, a first IR image captured by the first IR camera, and a second IR image captured by the second IR camera; associate the integrated IR image with an optical image captured by the optical camera; and generate an intra-operative 3D image based on the association of the integrated IR image with the optical image.

In some embodiments, the surgical device may be an endoscope. The endoscope may include an optical light transmitter configured to project optical light toward the one or more anatomical objects. The memory may further store instructions thereon which, when executed by the processor, cause the system to display generated the intra-operative 3D image.

In embodiments, the system may include a third surgical instrument having a third IR camera. The first, second and third surgical instruments may be positioned such that each IR camera maintains a different field of view within the body of the patient.

In certain embodiments, the scanner is a first scanner and the system may further include a second scanner that is configured to transmit IR light at a different frequency than that of the first scanner. Additionally, or alternatively, the memory may further store instructions thereon which, when executed by the processor, cause the system to transmit IR light from the first scanner at a first frequency when the second scanner transmits IR light at a second frequency that is different from the first frequency and/or transmit IR light from the first scanner and the second scanner at interleaved timing with respect to the first scanner.

According to yet another aspect of the disclosure, a non-transitory computer readable storage medium stores a program which, when executed by a computer, causes the computer to: generate IR light images of IR light projected by a scanner and reflected off of an anatomical object, where each of the IR light images is captured by a plurality of IR cameras; determine parallax between the plurality of IR cameras and the scanner; associate the IR light images to create an integrated IR light image based upon the determined parallax; and associate the integrated IR light image with an optical light image of the anatomical object to generate a real-time, intra-operative 3D image of the anatomical object. The program, when executed by the computer, may cause the computer to generate the real-time, intra-operative 3D image and/or display the generated real-time intra-operative 3D image.

In embodiments, the program, when executed by the computer, causes the computer to generate a 3D point cloud based on the integrated IR light image. In embodiments, the point cloud can be rendered into a volumetric shape such as a mesh or other 3D construct. In some embodiments, segmented CT objects can be overlaid into the surgical field of view on anatomical objects. Additionally, or alternatively, the program, when executed by the computer, causes the computer to warp the optical light image onto the integrated IR image.

Other aspects, features, and advantages will be apparent from the description, the drawings, and the claims that follow.

BRIEF DESCRIPTION OF THE DRAWINGS

Various aspects and features of the disclosure are described hereinbelow with references to the drawings, wherein:

FIG. 2 is a front, perspective view, of a distal portion of an endoscope of the system of FIG. 1A;

FIG. 3C is a side view illustrating the system of FIG. 1B imaging an anatomical object within a body of a patient using variable frequency scanning;

DETAILED DESCRIPTION

Figure 1A:
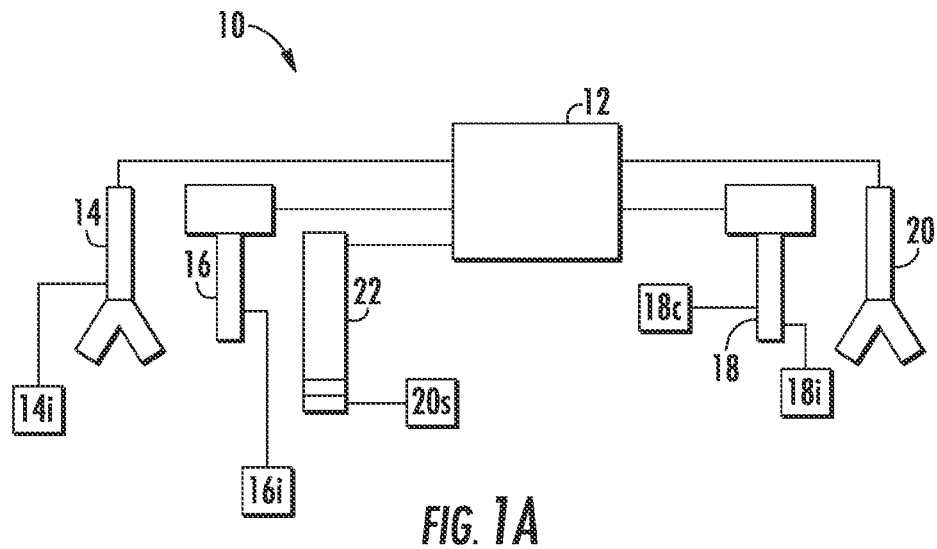
FIG. 1A is a schematic view of one embodiment of a system in accordance with the disclosure.

Aspects of the disclosed systems, devices and methods are described in detail with reference to the drawings, in which like reference numerals designate identical or corresponding elements in each of the several views. As commonly known, the term "clinician" refers to a doctor, a nurse, or any other care provider and may include support personnel. Additionally, the term "proximal" refers to the portion of structure that is closer to the clinician and the term "distal" refers to the portion of structure that is farther from the clinician. In addition, the term "cephalad" is used to indicate a direction toward a patient's head, whereas the term "caudad" indicates a direction toward the patient's feet. Further still, the term "medial" indicates a direction toward the middle of the body of the patient and the term "lateral" indicates a direction toward a side of the body of the patient (e.g., away from the middle of the body of the patient). The term "posterior" indicates a direction toward the patient's back, and the term "anterior" indicates a direction toward the patient's front. The phrases "in an embodiment," "in embodiments," or "in other embodiments" may each refer to one or more of the same or different embodiments in accordance with the disclosure. In addition, the terms "surgical devices," "surgical tools," "surgical instruments," and "surgical instrumentation" may be used interchangeably throughout the disclosure. Further, while reference may be made to elements in the singular, such distinction is intended only to simplify such description and is not intended to limit the subject matter of the disclosure. The term "target" used herein refers to tissue (either soft or hard) or areas/regions in the body of a patient that is designated as of interest for diagnosis or for therapeutic deliveries. Similarly, the term "anatomical feature" or its variants, refers to organs, tissue, vessels, or other discrete portions of the body of a patient. In addition, directional terms such as front, rear, upper, lower, top, bottom, and the like are used simply for convenience of description and are not intended to limit this disclosure.

In the following description, well-known functions or constructions are not described in detail to avoid obscuring the disclosure in unnecessary detail.

This disclosure is directed to systems and methods for creating and displaying a 3D endoscopic image from multiple cameras using optic and/or scanned images.

One method to create a 3D map of a surface is to use a scanner, which draws a pattern across the surface while capturing the distortion of the image. Distortion in the captured image is used to extract depth information to create a 3D map. This method uses a fixed projector that creates the scan pattern and a single dedicated camera to perform the image capture. The resultant information forms a point cloud of data points positioned in 3D space (e.g. x, y, z coordinates). This configuration of scanner and imager defines how the system can be constructed. The accuracy of the positional information derived from this system is dependent on the parallax, namely, the distance and angle between the scanner field of view (FOV) and that of the camera(s), where larger distances and angles produce better results.

For a medical endoscope, the amount of parallax that can be achieved is limited by the physical properties of the endoscope, which must be linear in design to allow ease of insertion into trocars or body cavities. One implementation places a camera at the distal end of the scope and the scanner some distance back from the distal tip and projecting out the side of the endoscope body. By designing the FOV optics of the scanner and camera, overlap can be managed. This creates a gradient of parallax where there is little towards the distal tip but significant amounts away from the distal tip.

In order to address the issues described above, according to aspects of this disclosure, the camera is spatially removed, or otherwise separate, from the endoscope body. Instead of being associated with the endoscope, the imager is appended to one or more instruments or other objects that would have a view of a scan target. More particularly, the described systems and methods to image objects or targets in an in vivo scene utilize one or more scanners that project onto a target in vivo, while cameras are arrayed in vivo in different positions relative to one another and the scanner, thereby capturing different aspects (e.g., different perspectives) of the same scene. The data acquired is processed by the disclosed system to generate an intra-operative 3D image. An exemplary implementation would be to attach a camera to each laparoscopic instrument and trocar to provide multiple imagers simultaneously observing the scan target where each camera provides scene information.

This approach has multiple advantages over the traditional self-contained endoscopic design, which includes both the scanner and camera on the same device, and therefore has limited parallax. Placing a camera on each surgical instrument improves the ability to get wide parallax between the camera and scanner due to the natural separation between the instrument(s) and the endoscope. It should, of course, be understood that an imaging camera may still be provided on the endoscope at the distal tip adjacent to the scanner to support traditional monocular vision when no camera-supported instrument is in use.

Providing more than one camera-equipped instrument with a FOV overlapping the scanner's FOV allows multiple views from multiple angles to be collected simultaneously. Viewing the IR light output by the scanner from multiple angles via overlapping instrument camera FOVs increases the accuracy of the generated 3D point cloud and decreases the number of blind spots where a specific camera is blocked by an intervening structure from a portion of the scanner's FOV.

This can be extended to replacing some cameras with scanners or placing a scanner/camera pair on each instrument. This allows scanning and imaging from multiple directions simultaneously, speeding the ability to fully capture a scene in 3D with a decrease in the number of areas left unscanned due to intervening structures or temporary changes in surgical environment (e.g., smoke from ablation) interfering with a sole scanner or camera FOV. Because the level of detail increases as the scanner approaches a structure, a default zoom mode becomes available in the specific area covered by the instrument's FOV. In order to avoid interference between scanners, each could use a different frequency of light or interleaved timing.

FIG. 1A shows one embodiment of an endoscopic system, generally referred to as system 10, which is configured to generate a 3D spatial map of a surgical site and/or one or more anatomical objects. Endoscopic system 10 includes a computing device 12 that is in electrical communication with any number or type of surgical instrumentation such as first, second, third, and fourth surgical instruments 14, 16, 18, and/or 20, etc., and an endoscope 22, which may be a 3D endoscope. The surgical instruments 14, 16, 18, and 20 can include any suitable surgical instrument such as an electrosurgical forceps or pencil coupled to a generator (not shown), a surgical stapler, grasper, stitching device, catheter, endoscope, access portal/trocar, or the like. Each of surgical instruments 14, 16, 18 includes an imager in the form of an IR camera configured to capture infrared light. For instance, surgical instrument 14, which may be in the form of forceps, includes IR camera 14$i$. Similarly, surgical instrument 16, which may be in the form of a trocar through which forceps passes, includes IR camera 16$i$. Likewise, surgical instrument 18, which may be in the form of an access portal through which a grasper passes, includes IR camera 18$i$. Any of the disclosed surgical instruments may alternatively or additionally include an optical camera such as optical camera 18$c$ coupled to surgical instrument 18. Endoscope 22 includes an optical camera 22$c$, an IR light scanner 22$s$, and a light source 22$l$ (see FIG. 2).

Figure 1B:
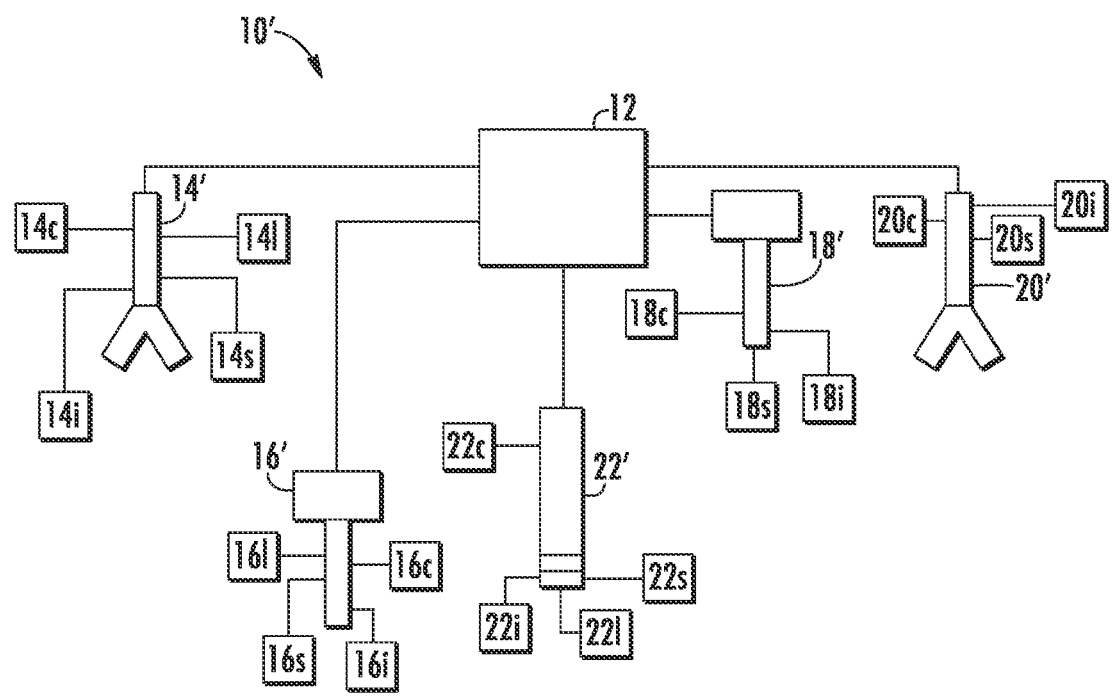
FIG. 1B is a schematic view of another embodiment of a system in accordance with the disclosure.

FIG. 1B shows another embodiment of an endoscopic system, generally referred to as system 10', which includes computing device 12 and surgical instruments 14', 16', 18', 20', and 22', each of which may be an endoscope. One or more of surgical instruments 14', 16', 18', 20', 22' can each include scanners (e.g., scanners 14$s$, 16$s$, 18$s$, 20$s$, 22$s$), optical cameras (e.g., 14$c$, 16$c$, 18$c$, 20$c$, 22$c$), light sources or optical light transmitters (e.g., 14$l$, 16$l$, 22$l$), or combinations thereof, and which may be arranged in any suitable configuration on one or more of the surgical instruments.

Figure 5:
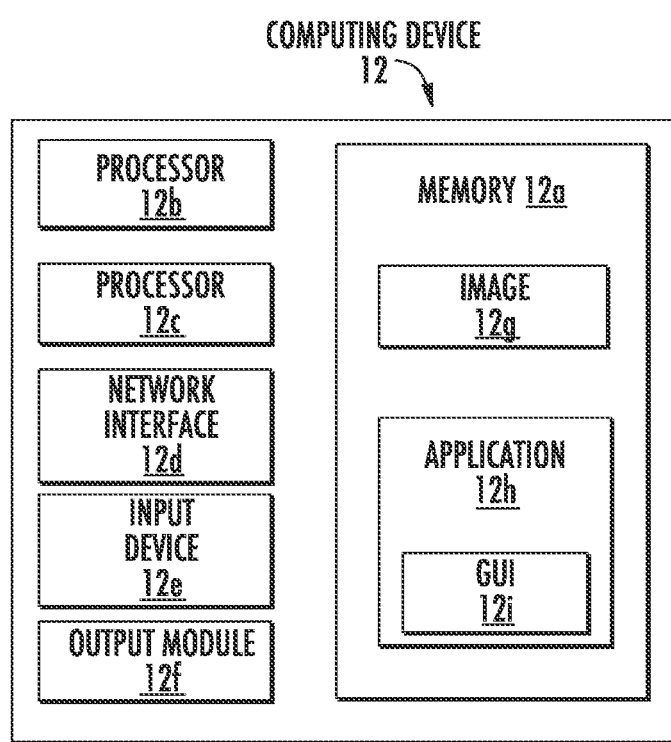
FIG. 5 is a block diagram of a computing device of the systems of FIGS. 1A and 1B.

FIG. 5 illustrates a simplified block diagram of computing device 12. Computing device 12 may include a memory 12$a$, a processor 12$b$, a display 12$c$, a network interface 12$d$, an input device 12$e$, and/or an output module 12$f$. Memory 12$a$ may store one or more applications 12$h$ and/or image data 12$g$. Application 12$h$ (which may be a set of executable instructions) may, when executed by processor 12$b$, cause display 12$c$ to present a graphical user interface (GUI) 12$i$ based on GUI instructions and/or perform cause processor 12$b$ to perform any other operation associated with the instructions stored thereon. Application 12$h$ may also provide the interface between one or more components of the system (e.g., one or more of the surgical instruments) and the computing device 12, through, for instance, Bluetooth and/or Wi-Fi. GUI 12$i$ may be displayed on display 12$c$ during the performance of any of the disclosed methods. Display 12$c$ may include procedural data that may be displayed via GUI 12$i$ such as the state of the patient "P" during the surgical procedure (e.g., heart rate, blood pressure, etc.) and/or the state of one or more the surgical instrumentation (e.g., operative, engaged, in error, or current operating parameters or modes), etc. Display 12$c$ may include AR/VR headsets.

Memory 12$a$ may include any non-transitory computer-readable storage media for storing data and/or software (instructions) executable by processor 12$b$ and which controls the operation of computing device 12 and/or various components of the system, when in communication with the components (e.g., with the optical cameras, light sources, scanners, IR cameras, etc.). In embodiments, memory 12$a$ may include one or more solid-state storage devices such as flash memory chips. Alternatively, or in addition to the one or more solid-state storage devices, memory 12$a$ may include one or more mass storage devices connected to processor 12$b$ through a mass storage controller (not shown) and a communications bus (not shown). Although the description of computer-readable media contained herein refers to a solid-state storage, it should be appreciated by those skilled in the art that computer-readable storage media can be any available media that can be accessed by processor 12$b$. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by computing device 12.

Network interface 12$d$ may be configured to connect to a network such as a local area network (LAN) including a wired network and/or a wireless network, a wide area network (WAN), a wireless mobile network, a Bluetooth network, and/or the Internet. Input device 12e may be any device through which a user may interact with computing device 12, such as, for example, a mouse, keyboard, foot pedal, touch screen, and/or voice interface. Output module 12f may include any connectivity port or bus, such as, for example, parallel ports, serial ports, universal serial busses (USB), or any other similar connectivity port.

Any of the disclosed scanners, such as scanner 22s, includes a structured light (or laser) scanner. The structured light scanner may employ infrared light so as to avoid interference from visible light sources, although it is contemplated that the structured light scanner may emit light in the visible spectrum, or any other wavelength or frequency band, depending upon the tissue being scanned during the procedure. In embodiments, light may be provided in a range of visible or IR spectrum. For instance, in the visible spectrum a frequency band may be the entire visible spectrum (e.g., white light) or a specific color frequency (e.g., green). The structured light source is selectively positionable in one or more positions, which may be predetermined, relative to one or more cameras (e.g., IR cameras 14i, 16i, 18i, and/or optical cameras 16c, 18c) of the disclosed systems (e.g., systems 10, 10'). The structured light source enables the calculation of the exact location of the intersection between the light ray from the structured light source and the one or more cameras of the system. This information can be scanned as single points, lines, or arrays to create topologic maps of surfaces. In embodiments, the structured light source is that of a light emitting diodes (LED) or LED infrared laser that is dispersed into a scan pattern (e.g., line, mesh, dots, etc.), by rotating mirror, beam splitter, diffraction grating, and/or panning. In one embodiment, the structured light source may be an LED laser having collimated light. The laser scanner will enable visualization systems to achieve accurate surface maps of an anatomical object such as the lung needed in order to match preoperative computed images to the operative image generated by one or more cameras of the disclosed systems. In embodiments, a clinician may enter in commands or control a structured light pattern projected from any of the disclosed scanners using any suitable user input device (e.g., touchscreen, mouse, keyboard, or the like).

The IR light may also be projected in a predetermined pattern (e.g., a grid or shaped pattern) and/or may be projected toward a target such as tissue surface, which may include the target, surrounding tissue, or other tissue within the body of the patient "P" and surgical objects the like. The IR light may be configured to strike the target and/or surrounding tissue. One or more of the beams may be projected at varying distances from one another, to increase or decrease the precision of each IR image. For example, in embodiments, the IR light may form one or more patterns such as preselected geometric images (e.g., stripes, random or structured placements of dots). Based on the desired level of accuracy, the patterns may be varied in complexity, having greater amounts of angles, positioned closer to one another, etc. Patterns may also be selected to optimize later analysis of the IR light once captured.

Any of the disclosed optical cameras may be visual-light optical cameras, such as a charge-coupled device (CCD), complementary metal-oxide-semiconductor (CMOS), N-type metal-oxide-semiconductor (NMOS), or other suitable camera known in the art. In embodiments, an optical camera may be a CCD camera having a resolution of 1080p. In some embodiments, any of the disclosed systems may include a digital filter (not shown) or a filter having narrow band optical grating (not shown) that inhibits extraneous light (e.g., visible) from distracting the clinician during a surgical procedure. In some embodiments, visible light is filtered from the image captured by one or more of the disclosed optical cameras and transmitted to the clinician such that any captured image is clear and free from extraneous light patterns. The optical light transmitters may be LEDs that emit white light, although any suitable light emitting device may be utilized. In some embodiments, the optical light transmitters may include RGB LEDs to provide the ability to generate an infinite range of different visible light spectrum. In some aspects of the disclosure, the optical light transmitters are configured to fade between and/or discretely switch between various subsets of the visible spectrum. In certain embodiments, the optical light transmitters may provide RGB, IR, UV, or combinations thereof (e.g., RGB and IR combination LEDs, RGB and UV combination LEDs, and/or IR and UV combination LEDs).

Any of the disclosed IR cameras may be CCD cameras capable of detecting IR light (for example, as reflected), although it is contemplated that the IR cameras may have sufficiently wide optical capture spectrum to detect visible light, such as visible green light or the like, depending upon the tissue being scanned. Specifically, visible green light contrasts with tissue having a red or pinkish hue enabling IR cameras to more easily identify the topography of the tissue. Likewise, visible blue light that is absorbed by hemoglobin may enable the system to detect vascular structures along with a vascular topology to act as additional reference points to be matched when aligning captured images.

It is contemplated that any of the disclosed cameras may be any thermographic camera known in the art, such as such as ferroelectric, silicon microbolometer, or uncooled focal plane array (UFPA), or may be any other suitable visible light camera such as a charge-coupled device (CCD), complementary metal-oxide-semiconductor (CMOS), N-type metal-oxide-semiconductor (NMOS), or other suitable camera where the light emitted from any of the disclosed scanners is in the visible or detectable spectrum.

In embodiments, any of the disclosed cameras, scanners, or transmitters may include one or more transparent protective covers (not shown) capable of inhibiting fluids or other contaminants from coming into contact with the disclosed cameras, scanners, or transmitters. In some embodiments, any of the disclosed cameras, scanners, or transmitters may include one or more coatings or layers with hydrophobic properties such as silicones or HDMSO Plasma depositions. In certain embodiments, the covers may include raised geometry that sheds, or washes body fluids ejected onto the cover.

In operation, a patient "P" (FIG. 3A) may be imaged using any suitable standard imaging device (not shown), such as MRI, ultrasound, CT scan, Positron Emission Tomography (PET), or the like, and those images may be stored within a memory 12a (see FIG. 5) of the computing device 12. In a thoracic procedure, for instance, after the patient "P" is imaged, the clinician penetrates tissue "T" of the body or chest of the patient "P" using one or more surgical instruments 16 (see FIGS. 1A, 1B), such as trocars or other suitable device access devices so that other surgical instruments such as endoscopes, graspers, forceps, etc. can be positioned in vivo.

For instance, a distal portion of an endoscope can be advanced through one trocar and a grasper can be advanced through another trocar so that the graspers and the forceps can be positioned in or adjacent to a surgical site such as the thoracic cavity of the patient "P."

Figure 4:
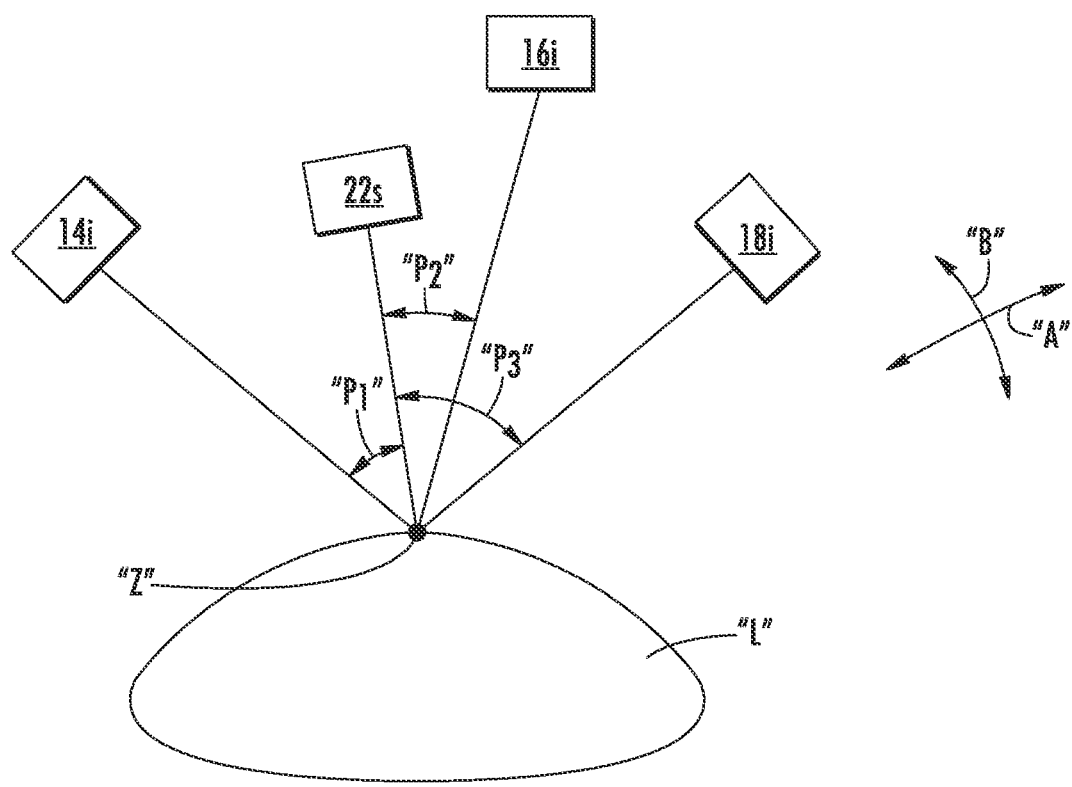
FIG. 4 is a schematic view illustrating parallax between a scanner and IR cameras of the systems of FIGS. 1A and 1B.

To enable the clinician to observe images on a display 12c (FIG. 5) of computing device 12, for instance in real-time, surgical instruments 14, 16, 18, 20, including endoscope 22, can be arrayed around an anatomical object such as a lung "L" so that the surgical instruments, namely cameras and/or scanners thereof, have different fields of view of the lung "L." For example, IR camera 14i of surgical instrument 14 can have a first field of view 14f (from a first perspective), IR camera 16i of surgical instrument 16 can have a second field of view 16f (from a second perspective), and IR camera 18i of surgical instrument 18 can have a third field of view 18f (from a third perspective). One or more of those fields of view may be wholly or partially inhibited by one or more surgical and/or anatomical objects such as objects "O1," "O2," and "O3." While one or more of the surgical instruments (e.g., IR camera 16i) may be selectively fixed in position for maintaining a constant field of view, such as to a rib "R" as illustrated by connector 16x, one or more other surgical instruments (e.g., IR cameras 14i, 18i, and/or optical cameras 18c, 22c) may be movably positioned in vivo to capture different and/or changing fields of view. Such movement, which may be in any direction such as in one or more of anterior, posterior, lateral, medial, caudal, cephalic, or the like directions, is illustrated by arrows "A" and "B" shown in FIG. 4 and may include panning and/or zooming.

Figure 6:
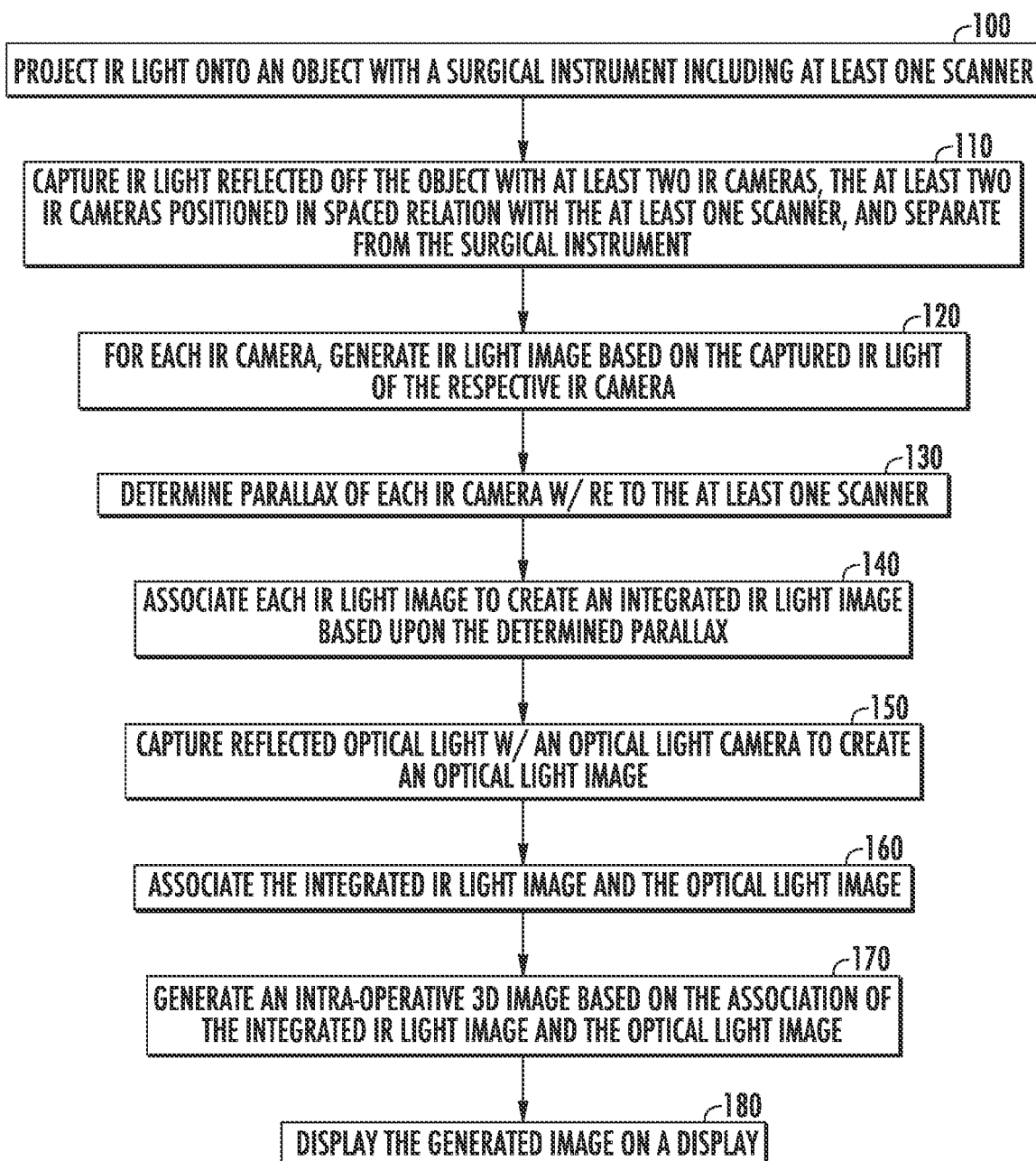
FIG. 6 is a flow chart of a method for imaging an anatomical object within a body of patient.
Figure 7:
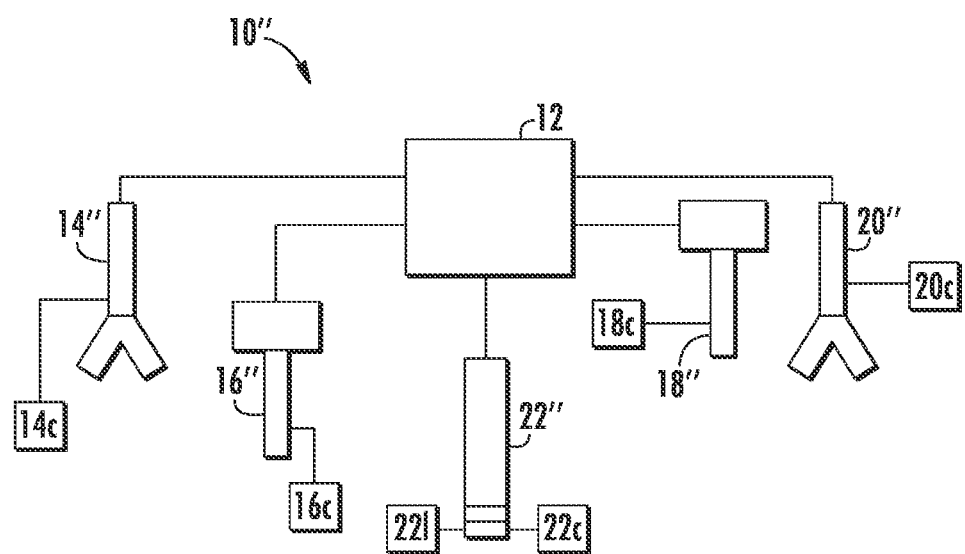
FIG. 7 is a schematic view of yet another embodiment of a system in accordance with the disclosure.
Figure 8:
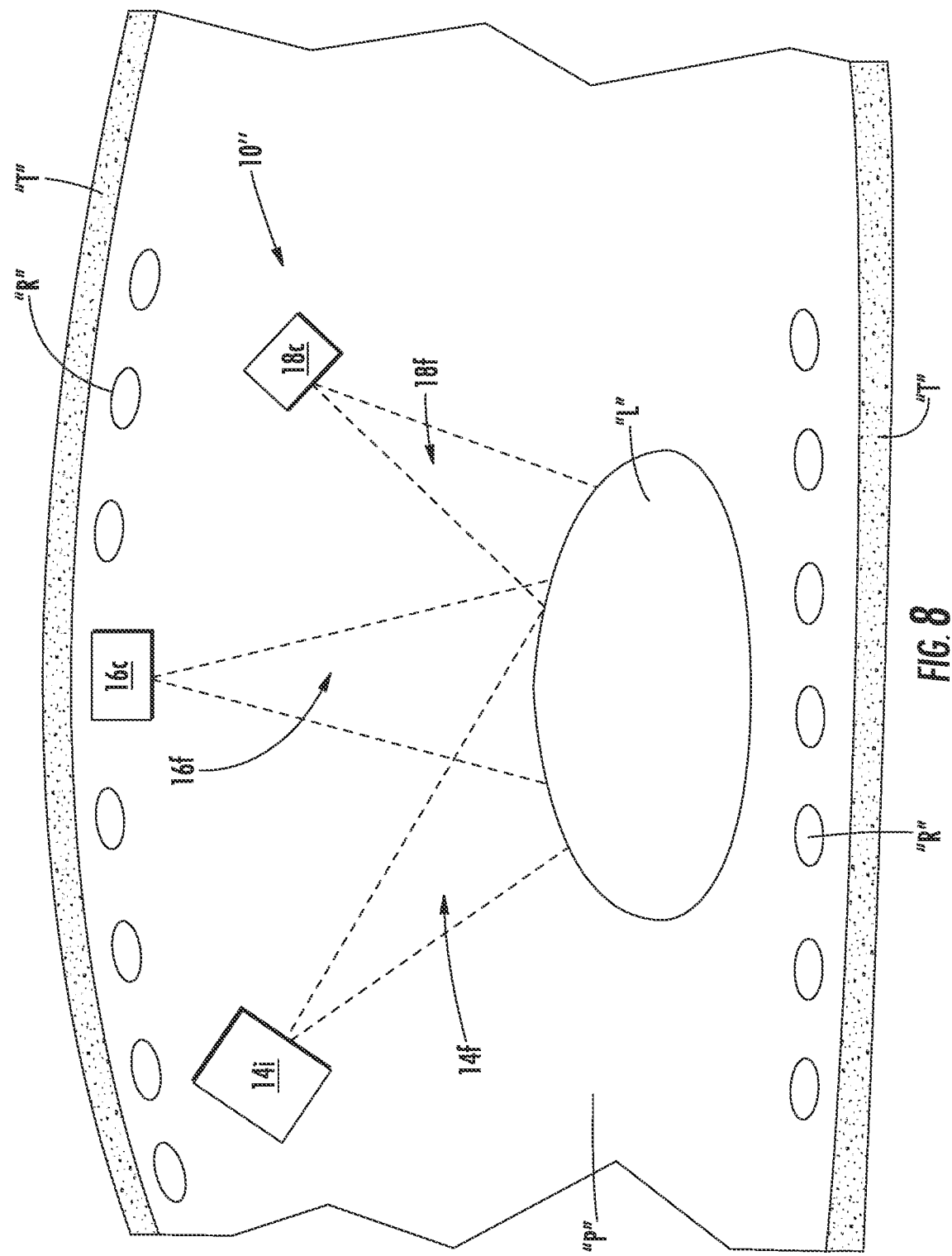
FIG. 8 is a schematic view of still another embodiment of a system in accordance with the disclosure.
Figure 9:
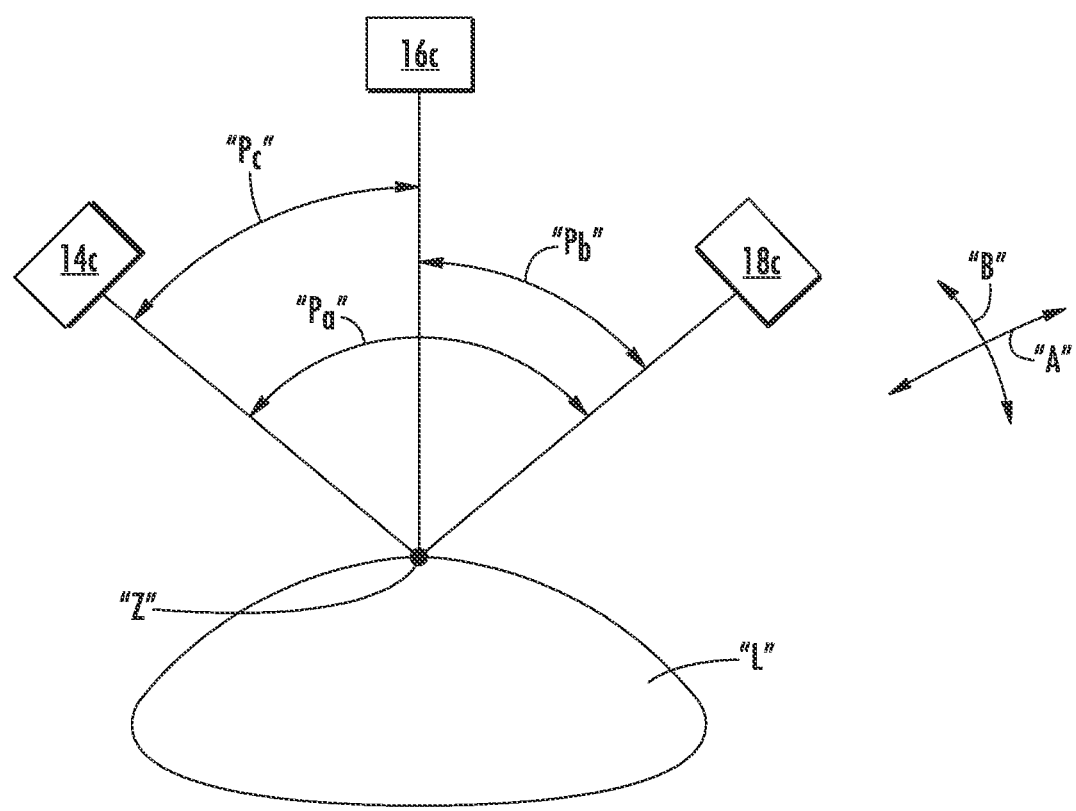
FIG. 9 is a schematic view illustrating parallax between optical cameras of the system of FIG. 8.

FIG. 6 shows a flowchart that outlines an exemplary method of imaging a surgical site and/or objects therein, generating an intra-operative 3D image and/or 3D model, and displaying at least one of the intra-operative 3D image and/or 3D model. While the method includes various steps described in a particular sequence, the described steps may be performed in a different order, repeated, and/or omitted without departing from the scope of the disclosure. Additionally, the below description of the method refers to various actions performed by the computing device 12, but these actions may be performed on various computing devices configured to operate in a similar manner, or by any component of the systems described herein. The actions performed may also occur in response to instructions stored in one or more memories 12a which are configured for execution on the one or more processors 12b of the computing device 12 (FIG. 5).

Figure 3A:
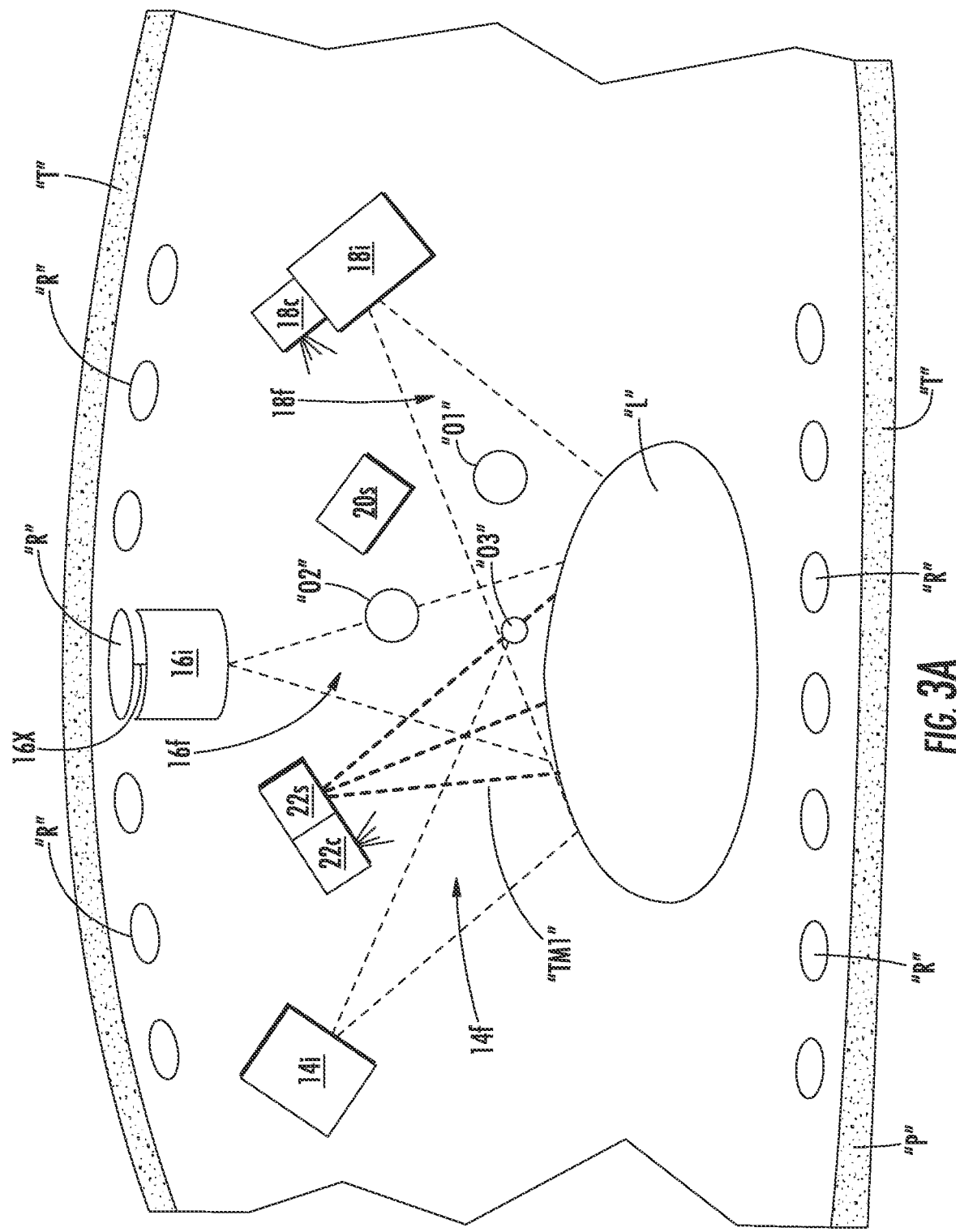
FIGS. 3A and 3B are progressive views illustrating the system of FIG. 1B imaging an anatomical object within a body of a patient using interleaved timing.
Figure 3B:
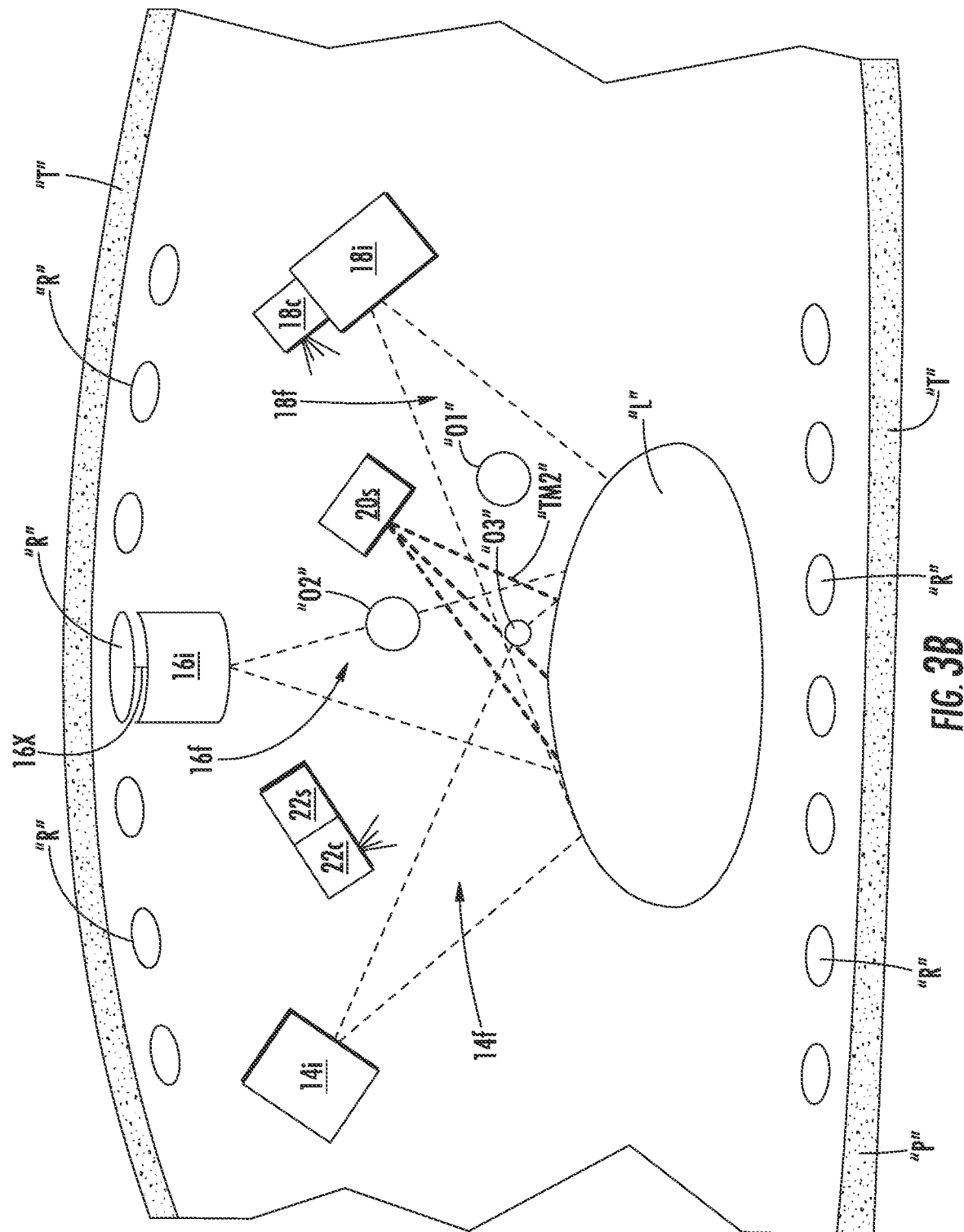

In step 100, to image a target such as an anatomical object within a body of a patient, such as the lung "L," infrared (IR) light (e.g., laser) is projected (e.g., a plurality of IR light beams or a large beam of IR light covering an entire viewing window) from one or more scanners of one of the disclosed systems, onto the target (e.g., an anatomical object) within the patient. The beams may be projected in any configuration or pattern (e.g., grid and/or other shape) and may be projected any number of distances, which may be one or more predetermined distances relative to the scanner and/or other beams. As illustrated in FIGS. 3A and 3B, the IR light may be projected at interleaved timing, where the interleave interval may be defined by computing device 12 and/or negotiated between instruments, and where a first scanner 22s projects the IR light for a first time period "TM1" and a second scanner 20s projects the IR light for a second time period "TM2." The time periods may be the same, may be different, may partially overlap or not, and/or may be successive. Scanners 20s, 22s may be configured to project the IR light at the same and/or different frequencies. In some aspects of the disclosure, the IR light may be projected by the same scanner in both time periods using the same and/or different frequencies, for instance, to prevent interference with optical light or each other. With reference to FIG. 3C, the first and second scanners 20s, 22s may project the IR light at the same time using the same and/or different frequencies, as indicated by the first frequency "Hz1" and the second frequency "Hz2" illustrated. Once the IR light contacts the target, light is reflected off the target toward one or more IR cameras in the patient "P."

While the systems and methods described herein may refer to the use of IR light to determine distance and optical light to capture optical images for subsequent analysis and display, the use of IR light and optical light may be interchanged, for instance to create light patterns and/or to illuminate portions or an entirety of a surgical space. Both the IR light and the optical light may be received by multiple sensors, to enable stereoscopic imaging of the reflected light by the respective sensors configured to capture the light.

In step 110, two or more IR cameras capture IR light reflected off the anatomical object (not shown). The two or more IR cameras are positioned separate from the one or more scanners, for example, on different surgical instruments than surgical instruments supporting the one or more scanners. The two or more IR cameras are disposed in spaced relation with respect to the one or more scanners and may be arrayed about the anatomical object such that each IR camera has a different field of view with respect to the other IR cameras. The fields of view may be at least partially overlapping. In certain aspects, three or more separate IR cameras may be provided.

The IR light may be received as a plurality of points at varying distances from one another. With reference also to FIG. 5, the one or more IR cameras, in response to receiving the light reflected from target, transmit an image that includes the reflected light as IR image data to the computing device 12. The IR image data may be based on the varying amounts and locations of infrared energy detected (e.g., radiation). The computing device 12 stores the IR image data in the memory 12a of the computing device 12, and may store the IR image data in any suitable data structure such as a 2D array, 3D model, etc. In embodiments, storage and analysis of the IR image data may be referred to as a 3D array of distance measurements calculated based on the received IR image data by the computing device 12.

In step 120, for each IR camera, an IR light image is generated, for instance by the computing device 12, based on the captured IR light of the respective IR camera.

In step 130, parallax of each IR camera relative to the other IR cameras and/or scanner(s) (e.g., distance and angle) can be determined, for example by computing device 12 and/or any number or type of position sensors (not shown) or tracking software coupled to the respective IR cameras (or instruments thereof), based on the position of the respective IR cameras with respect to the one or more scanners and each other (see, for example, the different parallax "P1," "P2," and "P3" with respect to a point "Z" on the lung "L"). For instance, the positioning sensors may include electromagnetic sensors. In some embodiments, the various sensors may be separate and distinct components with associated hardware and/or software or may be part of a commercial platform such as the Intel® RealSense™ technology system developed by Intel. Alternatively, or additionally, other external imaging modalities such as MRI, Fluoroscopy, etc., RFID, or the like may also be used.

In particular applications, the positioning of the surgical devices, or components thereof, can also be tracked by intraoperative instrument tracking systems for example electromagnetic (EM) navigation systems. The locational information obtained by the intraoperative instrument tracking system aids in simplifying the algorithms needed to produce large-scale spatial surface maps from segmental sized scans.

In step 140, the IR light images (e.g., some and/or all) are associated to create an integrated IR light image based upon the determined parallax. In embodiments, the computing device 12 creates a 3D data point cloud from the processing (and converging) of data from each of the IR light images captured for creating the integrated IR light image. In embodiments, the 3D data point cloud can be provided in the form of an intra-operative 3D model. In embodiments, the intra-operative 3D model may be matched with a portion of a pre-operative 3D model and/or a pre-operative image data (e.g., points contained or otherwise associated with the pre-operative 3D model). Matching may occur by identifying certain fiducial markers in both the pre-operative 3D model and the intra-operative 3D model and, based on the matching, the pre-operative 3D model and the intra-operative 3D model may be aligned or otherwise associated with one another. The fiducial markers may be naturally occurring anatomic or mechanical and placed by a clinician before imaging by a CT or other modality. The computing device 12 generates a 3D model (e.g., the intra-operative 3D model), or a rendering of the 3D model for display on a 2D display (e.g., display 12c) based on the integrated IR light image data and may store the 3D model in the memory 12a. The 3D model may be stored in the memory 12a in any suitable data structure (e.g., a 2D array of distances from a common plane or a 3D array of points).

In step 150, the one or more optical light cameras (e.g., 20c, 22c) capture reflected optical light to create an optical light image. For instance, one or more optical light transmitters (e.g., light source 221) emit visible light that is reflected off the target and captured by the optical cameras 20c, 22c of one or more of the various surgical instruments. The optical light cameras convert the detected light into visible light data that is processed by the optical light camera(s) and/or the computing device 12 to form the optical light image. The optical light image data may be stored on the memory 12a of computing device 12. The projection of optical light by the one or more optical light cameras can be effectuated before, during, and/or after projecting IR light from the one or more scanners.

In step 160, the integrated IR light image is associated with the optical light image. For instance, integrated IR light image data is associated with the optical light image data stored in the memory 12a of the computing device 12 such that the integrated IR light image data and the optical light image data are combined and/or warped together. In embodiments, optical light image data can be associated with one or more of the IR light images and/or the integrated IR light image before, during, after, and/or instead of integrating the IR light images.

In step 170, an intra-operative 3D image (and/or 3D model) is generated based on the association of the integrated IR light image (or one or more of the IR light images) and the optical light image based on the combined or warped data of the IR and optical light image data. For instance, the computing device 12 maps the optical image data to corresponding points in the 3D model. These points may be mapped by aligning the optical light image data with the integrated IR image data (or one or more of the IR light images) (e.g., adjusting the pixels to account for the spatial difference and/or parallax between the one or more optical cameras and the one or more IR cameras) and, once aligned, associating the optical image data with the integrated IR image data (or one or more of the IR light images). For example, when the optical image data is captured as a 2D array of points, the 2D array of points may be advanced or otherwise projected toward the 3D model, with each corresponding point of the 3D model (along the surface of the objects contained therein) associated with the point in the 2D array from the optical image data. Each point may include image data such as color value, luminance, chrominance, brightness, etc. As subsequently captured optical image data is mapped to the 3D model, the earlier-captured optical image data may be compared to the most-recently captured optical image data and updated as is necessary. Once the optical image data is mapped to the integrated IR image data (or one or more of the IR light images), the computing device 12 may generate the intra-operative 3D model (or, where a 2D display is available, a 2D rendering of an intra-operative 3D image) to be displayed on the display 12c of the computing device 12 based on the mapping of the optical image data to the integrated IR image data (or one or more of the IR light images). In embodiments, once the intra-operative 3D model and/or the intra-operative 3D image is generated, the computing device 12 causes the output module 12f to output the 2D and/or 3D image.

In step 180, the generated image is displayed on the display 12c of the computing device 12. The generated image can include any number of images captured and/or combined and/or otherwise stitched together to provide a 3D spatial map of the anatomical object, portions, or an entirety of the surgical site, which may include any anatomy and/or objects disposed therein (e.g., surgical tools). Imaging may be effectuated one-time and/or repeated (e.g., continuously) so as create a video stream of intra-operative 3D images. In aspects of the disclosure, axial CT image slices may be included. In particular, with location identified in the 3D model, one could determine which slice of the CT image a special point on the 3D model came from so that the axial CT image can be superimposed into the view. The image would be warped in perspective to denote both the rotation of the FOV to the normal of the CT image and also the depth as one side of the CT image will be closer to the FOV than the other. The user could scroll through the axial views and the view would continue to display a single CT image slice overlaid or inserted into the FOV.

FIGS. 7-10 show another embodiment of an endoscopic system, generally referred to as 10", which is similar to systems 10 and 10', but is configured to generate a 3D spatial map of a surgical site and/or one or more anatomical objects without any scanners.

Traditional 3D or stereoscopic endoscopes utilize optical ports located adjacent to each other on the distal endoscope tip and a crude 3D image is created from the small parallax between the ports. Placing a camera on each instrument, according to this disclosure, provides significantly wider parallax and allows for accurate measurement of object location within the overlapping FOVs.

More particularly, endoscopic system 10" includes a variety of surgical instruments (e.g., instruments 14", 16", 18", 20", and 22") having optical cameras that are arrayed about an anatomical object and that capture visible light images at different fields of view such as fields of view 14f, 16f, and 18f that may at least partially overlap. A computing device 12 (including memory 12a for storing captured or predetermined data) coupled to the optical cameras associates (e.g., via one or more processors 12b thereof) the visible light images to create an integrated image for displaying on a display 12c (FIG. 5). In embodiments the scanner(s) may be configured to generate a stripe where the beam moves through a defined arc length as a standard that all cameras could observe, and the length can be used to calibrate the ad hoc coordinate system (e.g. not using EM navigation system or similar) being created from the multiple cameras.

Figure 10:
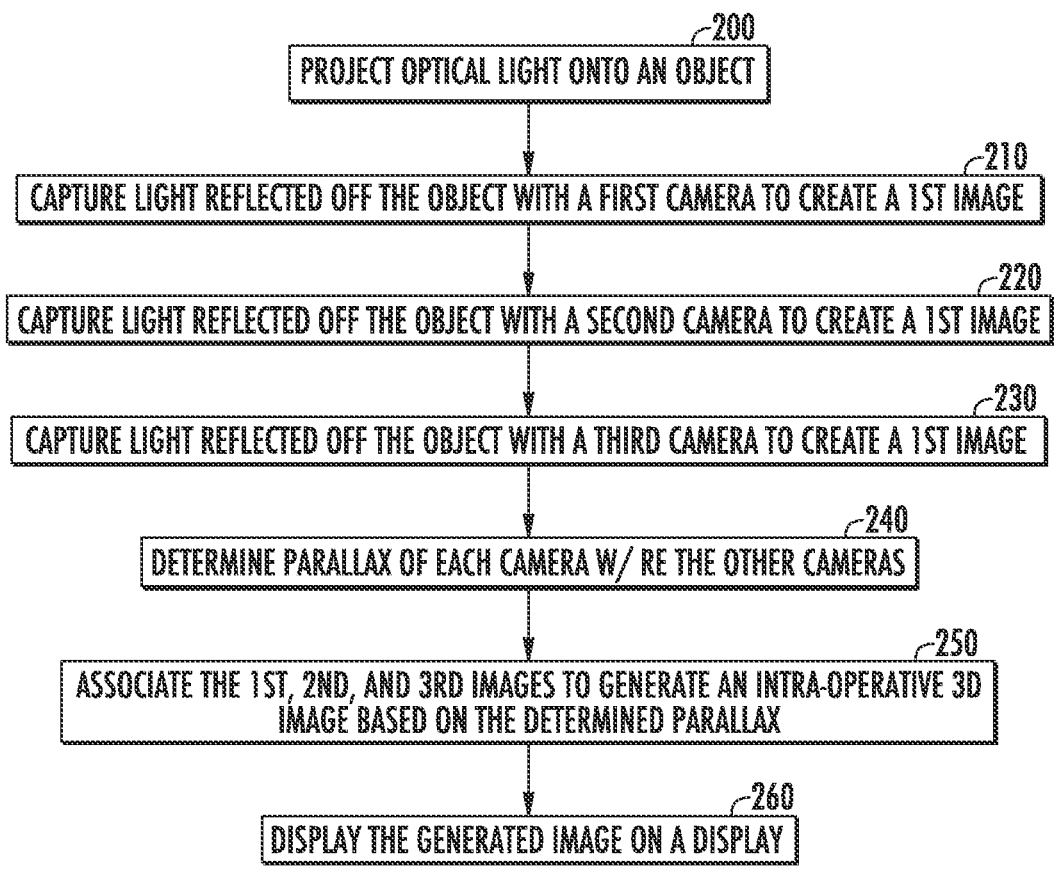
FIG. 10 is a flow chart of a method for imaging an anatomical object within a body of patient.

FIG. 10 shows a flowchart that outlines an example method of imaging a surgical site and/or objects therein, generating an intra-operative 3D image and/or a 3D model, and displaying at least one of the intra-operative 3D image or the 3D model. While the method includes various steps described in a particular sequence, the described steps may be performed in a different order, repeated, and/or omitted without departing from the scope of the disclosure. Additionally, the below description of method refers to various actions performed by the computing device 12, but these actions may be performed on various computing devices configured to operate in a similar manner, and/or any component or combination of components of the systems described herein. The actions performed may also occur in response to instructions stored in one or more memories 12a which are configured for execution on the one or more processors 12b of the computing device 12 (FIG. 5).

In step 200, to image an anatomical object within a body of a patient, such as the lung "L," optical light is projected from one or more optical light transmitters, such as light source 221 of endoscope 22" of system 10", onto the target (e.g., an anatomical object) within the patient.

In steps 210-230, first, second, and third cameras 14c, 16c, 18c of system 10", respectively, capture light reflected off the target to create respective first, second, and third images.

In step 240, parallax of each camera (e.g., distance and angle) is determined with respect to the other cameras, for instance, by the computing device 12 and/or any number or type of position sensors (not shown) and/or tracking software coupled to the respective cameras and/or instruments.

In step 250, the first, second, and third images, namely the corresponding data thereof, are associated (e.g., processed by the computing device 12) to generate an intra-operative 3D image and/or 3D model based on the determined parallax.

In step 260, the generated image is displayed on a display 12c. The generated image can be correlated to any pre-operative imaging. The generated image can include any number of images that can be combined or otherwise stitched together and may be provided as a 3D spatial map of the anatomical object or at least portions of the surgical site including any anatomy or objects disposed therein (e.g., surgical instrumentation).

According to aspects of the disclosure, generated 3D images may be associated with pre-operative 3D models generated from pre-operative image data. More particularly, the application 12h, during execution, may cause computing device 12 to store the image data associated with the generated 3D image at a corresponding location in the 3D model. This association may enable computing device 12 to update images generated during, for instance, EM navigation, or display the intra-operative 3D model (in embodiments, the pre-operative 3D model) generated during planning or review phases of surgical procedures.

In certain embodiments, the components of the disclosed surgical systems may be positionable by a robotic system. The robotic system can provide precise six-axis orientation of the surgical instruments of the disclosed systems in a similar manner to the navigation systems but benefited by active positioning as well as locational knowledge of the surgical instruments within the patient. As can be appreciated, the robotic system may be utilized to autonomously move the surgical instruments to complete imaging of larger areas or whole organs.

More specifically, the systems, and/or components thereof, described herein may be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the surgical instruments disclosed herein while another surgeon (or group of surgeons) remotely controls the surgical instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, endoscopes, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

It is contemplated that the surgical instruments described herein may be positioned by the robotic system and the precise position of the endoscope transmitted to the computer to construct the 3D image of the scanned organ or operative field. The robotic system has the ability to autonomously scan the surgical field and construct a complete 3D model of the field to aid the surgeon in directing the robotic arms or to provide necessary 3D information for the robotic system to further conduct surgical steps autonomously. In embodiments, where the surgical instruments include a camera and/or a structured light source that are independent of one another, the robotic system may direct the camera and a structured light source separately. The robotic system provides the relative coordinates between respective surgical instruments needed to triangulate points in the structured light and/or camera views to construct a 3D surface of the operative field.

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 11:
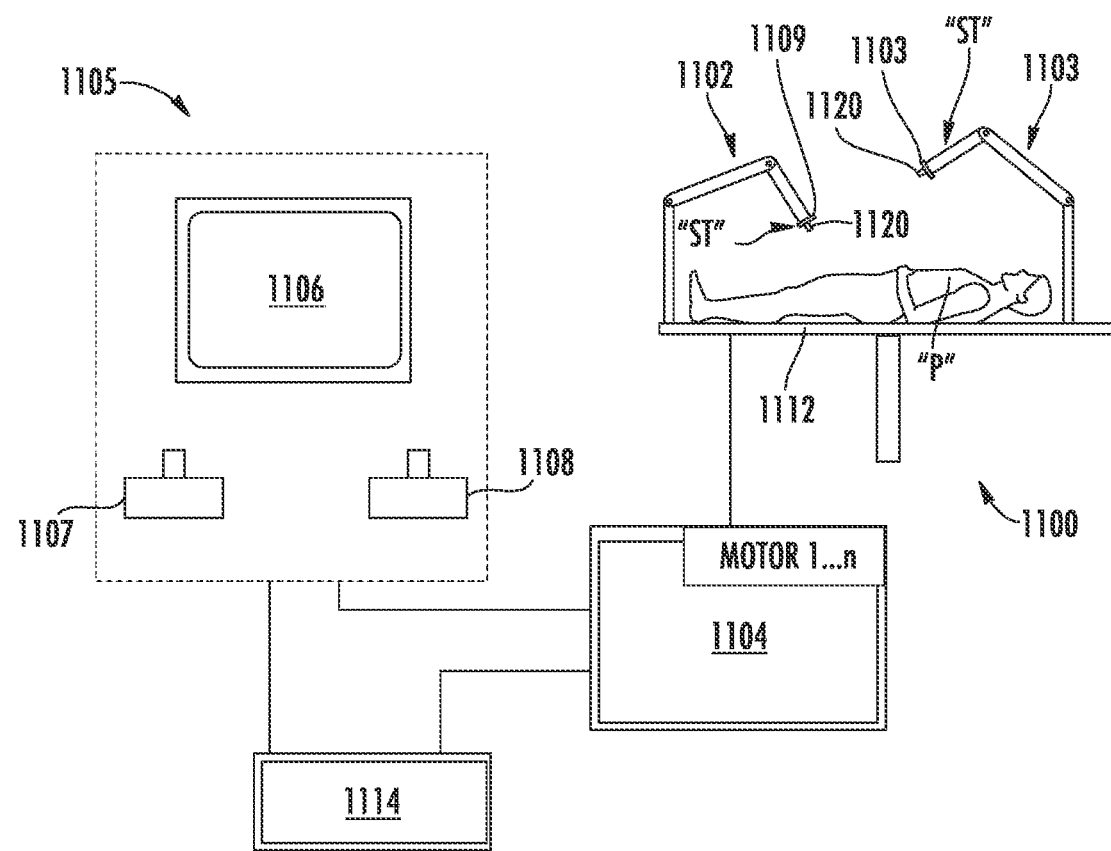
FIG. 11 is a schematic illustration of a robotic surgical system configured for use with the systems and methods of the disclosure.

Referring to FIG. 11, a medical work station is shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical instrument or surgical tool "ST" supporting an end effector 1100, in accordance with any one of several embodiments disclosed herein.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient "P" lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A surgical tool (including an end effector 1100) may also be attached to the additional robot arm. Medical work station 1000 may include a database 1014, in particular coupled to with control device 1004, in which are stored, for example, pre-operative data from patient/living being "P" and/or anatomical atlases.

One aspect of the disclosure is directed to an endoscopic system that supports organ matching to preoperative images, for example, images of a lung, other anatomy or anatomical features within a surgical site. The endoscopic system can provide both visual imaging and surface mapping for providing 3D models or 2D renderings of a 3D image (where a display is a 2D display). The endoscopic system includes surgical instrumentation that can be used to generate a 3D spatial map. The endoscopic system includes a computing device that utilizes the 3D spatial map to provide enhanced navigational guidance.

One advantage of the disclosure is to enable 3D surfacing of organs and other anatomical features and objects in a surgical site, which can be matched to preoperative computational imaging needed for operative guidance to target lesions with particular special knowledge of adjacent structures and anatomic boundaries such as in sublobar resection or lung cancer as well as overlay of pre-surgical planning information such as planned resection lines. Primary use for this system is thoracic, but this system can be utilized, or modified for use, in connection with deep pelvic surgery, rectal surgery, or other surgical applications.

The systems and methods described herein may be useful in various surgical procedures in which a patient is being diagnosed and/or treated, e.g., in cavities (insufflated or otherwise established), luminous structures, etc. For example, in an embodiment in which a clinician is performing a diagnosis of targets in a thoracic area of a patient, the disclosed systems and methods may be employed to assist during navigation of surgical instruments moving relative to anatomical features or targets within body. Specifically, the systems and methods described enable in vivo imaging for later display on an intra-operative 3D model or a two-dimensional 3D rendering (where a 3D display is not available). Additionally, the disclosed systems and methods may provide the clinician with the ability to view and/or determine various characteristics of anatomical features, structures, and/or other targets, as well as the position of one or more surgical devices, tools, and/or instruments relative to the body of the patient, as well as other surgical instrumentation disposed within or about the patient.

Persons skilled in the art will understand that the structures and methods specifically described herein and illustrated in the accompanying figures are non-limiting exemplary embodiments, and that the description, disclosure, and figures should be construed merely as exemplary of particular embodiments. It is to be understood, therefore, that the disclosure is not limited to the precise embodiments described, and that various other changes and modifications may be affected by one skilled in the art without departing from the scope or spirit of the disclosure. Additionally, it is envisioned that the elements and features illustrated or described in connection with one exemplary embodiment may be combined with the elements and features of another without departing from the scope of the disclosure, and that such modifications and variations are also intended to be included within the scope of the disclosure. Indeed, any combination of any of the disclosed elements and features is within the scope of the disclosure. Accordingly, the subject matter of the disclosure is not to be limited by what has been particularly shown and described.

What is claimed is:

1. A system for imaging within a body of a patient, comprising:
    a first surgical instrument;
    a second surgical instrument;
    a scanner configured to project IR light;
    a first IR camera coupled to the first surgical instrument;
    a second IR camera coupled to the second surgical instrument, wherein the first and second surgical instruments are separate from the scanner such that the first and second IR cameras are positioned in 3D spaced relationship with each other and the scanner projecting the IR light;
    an optical light camera; and
    a workstation operably coupled to the catheter and the biopsy tool, the workstation including a memory and a processor, the memory storing instructions, which when executed by the processor cause the processor to:
        generate IR light images of IR light projected by the scanner and reflected off of an anatomical object;
        capture a first IR light image with the first IR camera at a default zoom mode;
        capture a second IR light image with the second IR camera at the default zoom mode;
        determine parallax between the first and second IR cameras and the scanner, wherein the parallax is a distance and angle between the first and second IR cameras, a distance and angle between the first IR camera and the scanner, and a distance and angle between the second IR camera and the scanner;

associate the IR light images to create an integrated IR light image based upon the determined parallax;

align an optical light image of the anatomical object captured with the optical light camera with the integrated IR light image by adjusting pixels to account for the parallax between the optical light camera and the first and second IR cameras; and associate the integrated IR light image with the optical light image of the anatomical object to generate a real-time, intra-operative 3D image of the anatomical object.

2. The system according to claim 1, further comprising the memory storing thereon further instructions, which when executed by the processor, cause the processor to generate a 3D point cloud when associating the IR light images.

3. The system according to claim 1, further comprising a third IR camera, the first, second, and third IR cameras arrayed in the body of the patient, wherein the memory stores thereon further instructions, which when executed by the processor cause the processor to capture IR light with three IR cameras, each IR camera having a different field of view.

4. The system according to claim 3, further comprising the memory storing thereon further instructions, which when executed by the processor cause the processor to overlap the different fields of view.

5. The system according to claim 1, further comprising the memory storing thereon further instructions, which when executed by the processor cause the processor to capture IR light reflected off of the anatomical object within a first field of view associated with the first IR camera a second field of view associated with the second IR camera.

6. The system according to claim 5, further comprising the memory storing thereon further instructions, which when executed by the processor cause the processor to overlap the first and second fields of view.

7. The system according to claim 1, further comprising a second scanner configured to project IR light, wherein the memory stores thereon further instructions, which when executed by the processor cause the processor to project IR light from a second scanner onto the anatomical objected within the patient at a different frequency, interleaved timing, or combinations thereof, than that of the IR light projected by the scanner.

8. The system according to claim 1, further comprising the memory storing thereon further instructions, which when executed by the processor cause the processor to update the real-time, intra-operative 3D image of the anatomical object in real-time as new optical light images are captured by the optical light camera.

9. The system according to claim 2, further comprising the memory storing thereon further instructions, which when executed by the processor cause the processor to generate the 3D point cloud based on the integrated IR light image.

10. The system according to claim 1, further comprising the memory storing thereon further instructions, which when executed by the processor cause the processor to warp the optical light image into the integrated IR image.

11. A system of imaging within a body of a patient, comprising:
a scanner configured to project IR light;
a first surgical instrument;
a second surgical instrument,
a first camera coupled to the first surgical instrument;
a second camera coupled to the second surgical instrument, wherein the first and second surgical instruments are separate from the scanner such that the first and second IR cameras are positioned in 3D spaced relationship with each other and the scanner;
an optical light camera; and
a workstation operably coupled to the catheter and the biopsy tool, the workstation including a memory and a processor, the memory storing instructions, which when executed by the processor cause the processor to:
generate IR light images of IR light projected by the scanner and reflected off of an anatomical object;
capture a first IR light image with the first IR camera at a default zoom mode;
capture a second IR light image with the second IR camera at the default zoom mode;
determine parallax between the first and second IR cameras and the scanner, wherein the parallax is a distance and angle between the first and second IR cameras, a distance and angle between the first IR camera and the scanner, and a distance and angle between the second IR camera and the scanner;
associate the IR light images to create an integrated IR light image based upon the determined parallax;
align an optical light image of the anatomical object captured with the optical light camera with the integrated IR light image by adjusting pixels to account for the parallax between the optical light camera and the first and second IR cameras;
associate the integrated IR light image with the optical light image of the anatomical object to generate a real-time, intra-operative 3D image of the anatomical object; and
display the generated real-time, intra-operative 3D image on a display.

12. The system according to claim 11, further comprising the memory storing thereon further instructions, which when executed by the processor cause the processor to generate a 3D point cloud when associating the IR light images.

13. The system according to claim 11, further comprising a third IR camera, the first, second, and third IR cameras arrayed in the body of the patient, wherein the memory stores thereon further instructions, which when executed by the processor cause the processor to capture IR light reflected off of the anatomical object with three IR cameras, each IR camera having a different field of view.

14. The system according to claim 13, further comprising the memory storing thereon further instructions, which when executed by the processor cause the processor to overlap the different fields of view.

15. The system according to claim 11, further comprising the memory storing thereon further instructions, which when executed by the processor cause the processor to capture IR light reflected off of the anatomical object within a first field of view associated with the first IR camera and a second field of view associated with the second IR camera.

16. A system for imaging within a body of a patient, comprising:
a scanner configured to project IR light;
a first surgical instrument;
a second surgical instrument;
a first IR camera coupled to the first surgical instrument;
a second IR camera coupled to the second surgical instrument, wherein the first and second surgical instruments are separate from the scanner such that the first and second IR cameras are positioned in 3D spaced relationship with each other and the scanner;

an optical light camera;
a workstation operably coupled to the catheter and the biopsy tool, the workstation including a memory and a processor, the memory storing instructions, which when executed by the processor cause the processor to:
generate IR light images of IR light projected by the scanner and reflected off of an anatomical object;
capture a first IR light image with the first IR camera at a default zoom mode;
capture a second IR light image with the second IR camera at the default zoom mode;
determine parallax between the first and second IR cameras and the scanner, wherein the parallax is a distance and angle between the first and second IR cameras, a distance and angle between the first IR camera and the scanner, and a distance and angle between the second IR camera and the scanner;
associate the IR light images to create an integrated IR light image based upon the determined parallax;
align an optical light image of the anatomical object captured with the optical light camera with the integrated IR light image by adjusting pixels to account for the parallax between the optical light camera and the first and second IR cameras; and
associate the integrated IR light image with the optical light image of the anatomical object to generate a real-time, intra-operative 3D image of the anatomical object, wherein the real-time intra-operative 3D image of the anatomical object is updated in real-time as new optical light images are captured by the optical light camera.

17. The system according to claim 16, further comprising the memory storing thereon further instructions, which when executed by the processor cause the processor to generate a 3D point cloud when associating the IR light images.

18. The system according to claim 16, further comprising a third IR camera, the first, second, and third IR cameras arrayed in the body of the patient, wherein the memory stores thereon further instructions, which when executed by the processor cause the processor to capture IR light reflected off of the anatomical object with three IR cameras, each IR camera having a different field of view.

19. The system according to claim 18, further comprising the memory storing thereon further instructions, which when executed by the processor cause the processor to overlap the different fields of view.

20. The system according to claim 16, further comprising the memory storing thereon further instructions, which when executed by the processor cause the processor to capture IR light reflected off of the anatomical object within a first field of view associated with the first IR camera and a second field of view associated with the second IR camera.

* * * * *